United States Patent
Bruzzese

(10) Patent No.: US 11,154,525 B2
(45) Date of Patent: *Oct. 26, 2021

(54) PURIFIED COMPOSITIONS OF POLYUNSATURATED FATTY ACIDS, THEIR PREPARATION METHOD AND THEIR USE

(71) Applicant: Tiberio Bruzzese, Milan (IT)

(72) Inventor: Tiberio Bruzzese, Milan (IT)

(*) Notice: Subject to any disclaimer, the term of this patent is extended or adjusted under 35 U.S.C. 154(b) by 0 days.

This patent is subject to a terminal disclaimer.

(21) Appl. No.: 16/915,630

(22) Filed: Jun. 29, 2020

(65) Prior Publication Data

US 2020/0397734 A1 Dec. 24, 2020

Related U.S. Application Data

(63) Continuation of application No. 15/560,753, filed as application No. PCT/EP2016/056209 on Mar. 22, 2016, now Pat. No. 10,821,090.

(30) Foreign Application Priority Data

Mar. 26, 2015 (IT) .......................... MI2015A000441
Aug. 5, 2015 (IT) ........................ 102015000042303

(51) Int. Cl.
  *A61K 31/202* (2006.01)
  *A61K 31/201* (2006.01)
  *A61K 31/232* (2006.01)

(52) U.S. Cl.
  CPC .......... *A61K 31/202* (2013.01); *A61K 31/201* (2013.01); *A61K 31/232* (2013.01)

(58) Field of Classification Search
  None
  See application file for complete search history.

(56) References Cited

U.S. PATENT DOCUMENTS

| | | | |
|---|---|---|---|
| 4,792,418 A | 12/1988 | Rubin et al. | |
| 5,189,149 A | 2/1993 | Bruzzese et al. | |
| 5,656,667 A | 8/1997 | Breivik et al. | |
| 6,204,401 B1 | 3/2001 | Perrut et al. | |
| 7,541,480 B2 | 6/2009 | Bruzzese | |
| 8,021,874 B2 | 9/2011 | Anderson et al. | |
| 8,410,086 B2* | 4/2013 | Osterloh .............. | A61K 31/366 514/183 |
| 8,906,964 B2 | 12/2014 | Bobotas et al. | |
| 9,573,875 B2 | 2/2017 | Mougin | |
| 10,821,090 B2* | 11/2020 | Bruzzese .................. | A61P 1/04 |
| 2011/0033595 A1 | 2/2011 | Krumbholz et al. | |
| 2014/0323569 A1 | 10/2014 | Raman | |

FOREIGN PATENT DOCUMENTS

| | | | |
|---|---|---|---|
| EP | 0520624 A1 | 12/1992 | |
| EP | 1157692 A1 | 11/2001 | |
| WO | 2001010809 A1 | 2/2001 | |
| WO | 2009139641 A1 | 11/2009 | |
| WO | 2010118761 A1 | 10/2010 | |
| WO | 2014140864 A2 | 9/2014 | |

OTHER PUBLICATIONS

Maggie B. Covington, "Omega-3 Fatty Acids", 2004, American Family Physician, 70(1), pp. 133-140. (Year: 2004).*
Oh et al., "Management of Hypertriglyceridemia", 2007, American Family Physician, 75(9), pp. 1366-1371. (Year: 2007).*
Anonymous: "Evening Primrose Oil and Essential Fatty Acid Supplements—Efalex from Efamo", Jan. 1, 2014, retrieved from the Internet http://efamol.com/.
Breivik, H., "Chapter 5: Concentrates in: Beivik, H. Long-chain Omega-3 specialty oils", May 1, 2007, pp. 111-140.
Gunstone et al., "The component acids of lipids from marine and freshwater species with special reference to furan-containing acids", 1978, J. Sci. Food Agric. 29(6), pp. 539-550.
Hannemann et al., "The common occurrence of furan fatty acids in plants," 1985 Lipids 24(4), pp. 296-298.
International Preliminary Report on Patentability of PCT/EP2016/056209 dated Jun. 8, 2017.
International Search Report of PCT/EP2016/056209 dated May 13, 2016.
Lemke et al., "Synthesis and scavenging role of furan fatty acids", 2014, Proceedings of the National Academy of Sciences, 111(3), E3451-E3457 (www.pnas.org/cgi/doi/10.1073/pnas.1405520111).
Namal S., et al., "Concentration of docosahexaenoic acid (DHA) from algal oil via urea complexation", Journal of Food Lipids, vol. 7, No. 1, Mar. 1, 2000 pp. 51-61.
National Center for Biotechnology Information. PubChem Database. Ethyl icosapentate, CID +9831415, https://pubchem.ncbi.nlm.nih.gov/compound/9831415, Create Date: Oct. 25, 2006.
Ratnayake W. M., et al., "Preparation of omega-3 PUFA concentrates from fish oils via urea complexation", FETT-Lipid Fat Science Technology, vol. 90, No. 10, Oct. 1, 1988 pp. 381-386.
Schlenk et al., "Separation and stabilization of fatty acids by urea complex", 1950, J. am Chem. Soc., 72(11), pp. 5001-5004.
Senanayake, S.P.J.N. "Methods of concentration and purification of omega-3 fatty acids" 2, Separation, extraction and concentration processes in the food, beverage and nutraceutical industries, vol. 202, pp. 482-505.
Shahidi et al., "Omega-3 fatty accid concentrates: nutritional aspects and production", 1998, Trends in Food Science & Technology, 9(6), pp. 230-240.

(Continued)

*Primary Examiner* — My-Chau T. Tran
(74) *Attorney, Agent, or Firm* — Silvia Salvadori, P.C.; Silvia Salvadori

(57) ABSTRACT

The present invention refers to new purified compositions of long chain polyunsaturated fatty acids, or their salts or esters, characterized by being essentially free from other usually present—but structurally different—components, such as furan fatty acids, phytanic and pristanic acids, squalene, and some oligomers, as well as several "persistent" environmental pollutants, such as polychlorinated dibenzo-dioxins and polychlorinated dibenzo-furans, polychlorinated biphenyls, polybrominated diphenyl-ethers, polycyclic aromatic hydrocarbons, and others, which are also usually present and extremely toxic. The invention also refers to the purification method to obtain said compositions and the use thereof as food, food for special medical use, food and diet supplement, and drug.

6 Claims, 4 Drawing Sheets

(56) References Cited

OTHER PUBLICATIONS

Spiteller G, "Furan Fatty Acids: occurrence, synthesis and reactions. Are furan fatty acids responsible for the cardioprotective effects of a fish diet?", 2005, Lipids, 40(8), pp. 755-771.

Thitiphan Chimsook, "Supercritical fluid extraction of lipids and enrichment of DHA from freshwater fish processing wastes in Thailand", 2014, Advanced Materials Research, vols. 1004-1045, pp. 444-447.

Wendlinger et al., "High concentrations of furan fatty acids in organic butter samples from the german market", 2014 Journal of Agricultural and Food Chemistry, 62(34), pp. 8740-8744.

Written Opinion of PCT/EP2016/056209 dated May 13, 2016.

Yurawecz et al., "Furan fatty acids determined as oxidation products of conjugated octadecadienoic acid", 1995, Lipids 30(7), pp. 595-598.

* cited by examiner

PURIFIED COMPOSITIONS OF POLYUNSATURATED FATTY ACIDS, THEIR PREPARATION METHOD AND THEIR USE

This Non-Utility Application is a Continuation of U.S. Ser. No. 15/560,753 filed on Sep. 22, 2017, which is a U.S. national stage of PCT/2016/056209 filed on 22 Mar. 2016, which claims priority to and the benefit of Italian Patent Application No. MI2015A000441 filed on 26 Mar. 2015 and claims priority to and the benefit of Italian Patent Application No. 102015000042303 filed on 5 Aug. 2015, the contents of which are all incorporated herein by reference in their entireties.

DESCRIPTION

The present invention refers to new purified compositions of long chain polyunsaturated fatty acids (PUFAs), or salts or esters thereof, characterized by being essentially free from other usually present—but structurally different—components, such as furan fatty acids, phytanic and pristanic acids, squalene, and some oligomers, as well as several environmental pollutants defined as "persistent" (POPs, persistent organic pollutants), such as polychlorinated dibenzo-dioxins and polychlorinated dibenzo-furans, polychlorinated biphenyls, polybrominated diphenyl-ethers, polycyclic aromatic hydrocarbons, and others, which are also usually present and extremely toxic. The invention also refers to the purification method leading to said compositions and use thereof as food, food for special medical use, food and diet supplement, and drug, also including the use in animals and in aquaculture. The purification method consists in the treatment of a composition of PUFAs at the desired concentration, usually at high concentration, with an amount of urea suitable for obtaining a total complexation of all present PUFAs, and in the successive separation and isolation by filtration of the inclusion complex in urea of the purified PUFAs and of the solvent phase containing the other structurally different products and several "persistent" environmental pollutants.

BACKGROUND OF THE INVENTION

The long chain polyunsaturated fatty acids, containing 2-6 double bonds and 18 or more carbon atoms, are defined—depending on the position of the first double bond starting from the terminal methyl group—as "omega-6" (or n-6) and "omega-3" (or n-3).

Typical representatives of the two acid families are respectively linoleic acid (LA, C18:2 n-6) and alpha-linolenic acid (ALA, C18:3 n-3), defined as "essential" acids in that they are not synthesized in the body, and must be introduced with the diet.

Both of them undergo in the body a chain elongation and an increase of unsaturation degree by means of specific enzyme systems called elongases and desaturases.

The most known omega-6 acids are gamma-linolenic acid (GLA, C18:3 n-6) and arachidonic acid (ARA, C20:4 n-6) and the omega-3 acids defined as stearidonic acid (or moroctic acid, SDA, C18:4 n-3), eicosatetraenoic acid (ETA, C20:4 n-3), eneicosapentaenoic acid (C21:5 n-3), docosapentaenoic acid (or clupanodonic acid, DPA, C22:5 n-3), and particularly eicosapentaenoic acid (or timnodonic acid, EPA, C20:5 n-3, all cis) and docosahexaenoic acid (or cervonic acid, DHA, C22:6 n-3, all cis).

In all cases, the long chain polyunsaturated fatty acids are in variable ratios among themselves, and also in mixture with substantial quantities of saturated and monounsaturated acids such as oleic acid (C18:1 n-9).

In nature, these fatty acids can be found in different forms, as e.g. in phospholipids, etc., but more frequently they are found in form of oils (or fats), that is as esters with glycerol (glycerides). Omega-6 acids are particularly abundant in vegetable oils and seeds, whereas omega-3 acids and particularly EPA and DHA have prevalently marine origin and derive in particular from fish oils, even from aquaculture fish, or from krill oils or even from algae and other oleaginous microorganisms, or from "single cell fermentation", starting from selected strains of algae or other microorganisms.

These oils undergo usually some standard initial treatments, such as bleaching and neutralization, and then the present technology involves the concentration or the isolation from these complex mixtures of the most interesting components for pharmaceutical or alimentary use or dietetic supplements, as indeed EPA and DHA.

To this purpose, in a first phase the natural oils (the glycerides) are submitted to a mild hydrolytic procedure, e.g. by means of alcoholic potassium hydroxide, so obtaining the corresponding potassium salts and then the free acids and—if desired—the alkyl esters; alternatively and more often, a transesterification reaction is adopted, e.g. in the presence of aliphatic alcohols in excess, preferably C1-C3, and of an alkaline or acid catalyst, so directly obtaining the corresponding alkyl esters of the fatty acids, and from these—if desired—the relevant acids or salts.

Starting from recent years, said hydrolysis or alcoholysis procedures are carried out, beside the chemical route, also by enzymatic route, by means of selective lipases, even immobilized: this permits to operate in even softer reaction conditions, and further—because of the higher resistance of PUFAs to the enzymatic lysis, in comparison with saturated and monounsaturated acyls—it is also possible to isolate intermediate compositions of still partly acylated and PUFA enriched glycerols (see e.g. Kapoor R and Patil U K, Int Food Res J, 18, 493, 2011), to be submitted to hydrolysis or alcoholysis in a separate phase.

Coming back to the more general case, the first phase is usually followed by a treatment addressed to increase the concentration of the desired component, typically EPA or DHA or their mixture in preordered ratios, prevalently as ethyl esters or even as acids or salts, if preferred.

This treatment, often repeated more times and even combining various methods, involves several technologies, including essentially:

- distillation under high vacuum, usually molecular or short path distillation more suitable to limit the thermal degradation processes, arranging obviously to a proper fractioning;
- some chromatographic procedures, even under high pressure (HPLC), however more suitable to the laboratory scale or to analytical purpose;
- counter-current extraction;
- extraction with aqueous silver nitrate;
- extraction with supercritical fluids (SFE), usually with $CO_2$, even in combination with chromatographic processes (SFC) on preparative scale and with suitable stationary phase, more specific for the separation of single components, and performed both under continuous phase and through "batch" chromatography;
- however, in the case most general and industrially accepted, a reaction of urea complexation in alcoholic solution or other solvent and suspending agents known to the skilled man. It is known that in particular conditions urea may crystallize in hexagonal crystals, forming channels able to include the straight-chains of fatty acids, and that such inclusion essentially occurs with saturated and/or monounsaturated acids and esters, which are indeed endowed with straighter structures. The formed inclusion complex precipitates by cooling from the alcoholic solution and is removed by filtration, allowing then to recuperate a composition strongly enriched of polyunsaturated components, as e.g. EPA and DHA from the solution. Urea complexation constitutes therefore a "passive" process, in the sense that actually it occurs above all with the saturated and monounsaturated components, whereas PUFAs are recovered in enriched concentration from the mother liquors. Exhaustive reviews of these urea complexes and their preparation are those by Schlenk H, "Urea inclusion compounds of fatty acids", in: Progress in the Chemistry of Fats and Other Lipids Vol II (R T Holmar, ed.), Pergamon Press, New York, pp. 243-267 (1954), and by Swern D, "Techniques of separation. Urea complexes", in: Fatty Acids, Part 3 (KS Markley, ed.), Interscience, New York, pp. 2309-2358 (1963). Other more specific references will be given later on.

The various generic procedures for the enrichment of PUFAs are suitably summarized by Breivik H, "Concentrates", in: Long-Chain Omega-3 Specialty Oils (H Breivik, ed.), The Oily Press, Bridgwater, pages 111-130 (2007), and enrichment of PUFAs by enzymatic route, pages 146-155, hereafter reported as "Breivik 2007".

In general all these operations are concluded with a final phase of molecular distillation, addressed to remove residual low-boiling fractions, including the organic solvents introduced during the process, or to limit the presence of high-boiling fractions constituted in particular by "oligomers" (polar products derived from oxidation and degradation, and having a various degree of polymerization), which are always involved with any of the manipulations performed on these instable polyunsaturated substances, in agreement with European Pharmacopoeia (E.P.), monograph 1250. Such oligomers are dosed, differently from PUFAs which are analyzed with gaschromatography (GC), by means of "size-exclusion" or "gel-permeation" chromatography, and must be in fact till 1% maximum according to E.P.

An alternative to distillation is given by the use of fluids in "supercritical" conditions, which are used both for extractive purpose only, and for chromatographic purpose, e.g. for the gradual separation of EPA and DHA.

We also know from the literature that the natural polyunsaturated substances, and in particular the fish oils, are heavily polluted by substances of various nature, all harmful to the health in humans and animals if ingested as a drug or food or food supplement, and not even useful as a food for fish obtained from aquaculture.

Such substances are e.g. natural degradation products induced by the atmospheric agents or by the chemical manipulation, such as epoxides and peroxides, the last being potentially dangerous to the health in that endowed with aterogenic and mutagenic activities (e.g. Carroll K K, Cancer Res, 35, 3374, 1975), and such as the above mentioned oligomers and polymers.

"Natural" impurities, but anyway not structurally related to the compositions of fatty acids, are represented by cholesterol and several other vegetable and animal sterols, systematically present in seed oils and in oils of marine origin (PCT/WO 87/03899; Connor W E and Lin S E, Metab Clin Exp, 31, 1046, 1982).

Also some long-chain branched hydrocarbons such as squalene C30H50 and others are often present. Other Authors also report the systematic presence of a great number of cyclic derivatives of fatty acids, in quantities certainly not negligible, generically defined as furan fatty acids: all these substances do not result to have been studied at all under the toxicological aspect, or have been studied quite partly, and their presence is then totally unjustified because of their structure itself, in compositions which consist by definition of e.g. "omega-3 fatty acids", and under the standpoint of safety, in compositions addressed to the use as food or drug in humans. Many, but not all, of the furan fatty acids are clearly shown in the GC analysis of FIG. 1 drawn from the above mentioned monograph 1250 "Omega-3-acid ethyl esters 90" of E.P. 6.3, 2008 (see Enclosure), and their presence is still confirmed in the more recent monographs 07/2012:1250 of E.P. 8.0 and pages 4059-51 of USP 37 (Table 1 reporter here below) both still valid.

TABLE 1

| Identified ethyl ester | Relative retention time |
| --- | --- |
| Phytanic acid | 0.416 |
| C16:3 n-4 | 0.431 |
| C16:4 n-1 | 0.468 |
| C18:3 n-6 | 0.557 |
| C18:3 n-4 | 0.574 |
| C18:3 n-3 | 0.585 |
| C18:4 n-3 | 0.608 |
| C18:4 n-1 | 0.618 |
| Furan acid 5 | 0.691 |
| C19:5 | 0.710 |
| C20:3 n-6 | 0.720 |
| C20:4 n-6 | 0.736 |
| Furan acid 7 | 0.744 |
| C20:4 n-3 | 0.777 |
| Furan acid 8 | 0.783 |
| EPA | 0.796 |
| Furan acid 9 | 0.867 |
| C21:5 n-3 | 0.889 |
| C22:4 | 0.917 |
| Furan acid 10 | 0.922 |
| C22:5 n-6 | 0.939 |
| Furan acid 11 | 0.963 |
| C22:5 n-3 | 0.977 |
| DHA | 1.000 |

The chemical structure of these furan acids is clearly identified and reported in the book by H Breivik 2007 above mentioned, pages 130-132, and in the several bibliographic References there cited, even if it has been shown—and confirmed by ourselves—the additional presence of other di-methyl-substituted derivatives in the position 2 of the furan ring. In agreement with Breivik, a procedure for concentration of PUFAs involving urea and molecular distillation leads to a product with content of the various furan acids from equal to partly reduced (see above, Table 6), but never null.

Probably because of the high number of furan acids and of their different physical properties, as deducible from the different retention times and consequently from the different positions in the GC chromatograms, we are not aware of significant attempts to eliminate such components, which remain so present in the present commercial products.

Also usually present is phytanic acid, a long-chain branched saturated acid (tetramethyl-hexadecanoic acid, PhA), as shown in the same above Table 1 and in FIG. 1 herewith enclosed, drawn from monographs of E.P. 6.3 and E.P. 8.0, as well as USP 37, which is often joined with a lower homologous deriving from alpha-oxidation, that is pristanic acid (tetramethyl-pentadecanoic acid, PA), or salts or esters thereof. Differently from most other acids, phytanic acid cannot be metabolized through beta-oxidation, and e.g. in subjects with Refsum disease—having poor alpha-oxidation capacity—it accumulates in blood and tissues, leading to peripheral polyneuropathy, cerebellar ataxia, retinitis pigmentosa, anosmia and hearing loss.

The patent application US 2011/0033595 (WO 2011/018096), here recalled in its totality together with the References there cited, explains carefully that there is a general consensus to include in the western diet from 200 to 1000 mg per day of compositions based on EPA+DHA, but these compositions of marine and algal origin contain significant concentrations of PhA (see FIG. 3b, par. [0037], the same figure of our Encl.1), until 1000 ppm (0.1%) or more, so leading to serious health problems of millions of consumers [par.0001]. Besides citing the several diseases induced by the use of PhA ([0002] and [0003]), it is also explained that recent studies evidenced that the continuous use of PhA may induce several types of cancers, and that it is cytotoxic and pro-inflammatory, besides being a direct antagonist of EPA and DHA (par. [0004]-[0008]). To purify the PUFA mixtures from this particular component, said US2011/0033595 application describes a chromatographic fractioning procedure, with a liquid or a supercritical fluid eluent, by also isolating some fractions enriched in PhA, which are further purified to be suitable to cosmetic use by topical route and to other uses.

With reference to pristanic acid, it shares many of the serious toxic effects of PhA and it also accumulates in the body in several inherited illnesses as e.g. Zellweger syndrome.

The same application US 2011/0033595 describes as references the previous applications WO 01/10809, EP 1157692, U.S. Pat. No. 5,656,667 (par. [0025]-[0027]) and others, none of which appears to interfere, in their procedures and purposes, with the present application.

WO 01/10809 describes a procedure by which PUFAs in form of free acids, or esters or amides, particularly EPA and/or DHA, are recovered from urea adducts—such as those obtained as by-products during the working up of fish oils or other oils, and therefore mostly containing saturated and monounsaturated acids—by treatment with subcritical or supercritical fluids in determined temperature and pressure conditions. The purpose of the procedure is the recovery—in form partially concentrated—of a part of the PUFAs lost as by-products during the industrial production, without any purpose to purify them from foreign components.

EP 1157692 discloses compositions of fatty acids containing at least 80% by weight of EPA and DHA, and less than 3% of other particular omega-3 components. The procedure encompasses a transesterification process followed by suitable fractioning with urea and molecular distillation.

U.S. Pat. No. 5,656,667 describes a composition of fatty acids containing at least 80% by weight of EPA and DHA, and at least 1.0% of component C21:5 n-3, or at least 80% by weight of EPA and DHA in a ratio from 1:2 to 2:1, and at least 1.5% of other omega-3 acids different from EPA and DHA. Even in this case transesterification is followed by standard fractioning with urea and molecular distillation.

Also application US 2012/053242 (WO 2010/118761) describes a method to lower the content of PhA, according to which an oil of marine origin is saponified to give the corresponding salts, acidified to give the fatty acids, and such acids—which represent the only starting material of the procedure—are submitted to ultracentrifugation in a glycerol gradient at 10° C. and under vacuum of 27 Pa, usually at 100,000 g for 24-48 hours (claims 5, 6 of US 2012/053242), and then the glycerol gradient is subjected to crystallization to a temperature range between 0° C. and −57° C. obtaining a solid phase and a liquid phase, the last one containing polyunsaturated omega-3 acids with a content of PhA of less than 90 micrograms/g, which is separated by decantation. Claim 2 of US 2012/053242 discloses that these acids are also esterified to obtain the omega-3 acid triglycerides (ethyl esters are not obtained), while it is also claimed that the content of omega-3 acids is in the range of 65% to 99% by weight (claim 10 of US 2012/053242), the content of PhA is below 5 micrograms/g (claim 11 of US 2012/053242), the omega-3 acids comprise DHA in the range between 65% and 95% by weight (claim 14 of US 2012/053242) and EPA in the range of 5% to 35% by weight (claim 17 of US 2012/053242).

The other claims 19-61 of US 2012/053242 essentially refer to compositions for pharmaceutical and alimentary use, nutritional and food supplements, and methods of treatment in pathologies sensitive to the invention compositions.

The Description of US 2012/053242 describes widely the negative effects of PhA (and PA), as already reported by US 2011/0033595, also reporting several products introduced into the market and evidencing the high content of PhA in these products without significant correlation with the purity of the contained DHA (FIG. 3).

We have also noticed that in Example 3 of US 2012/053242, addressed to the analysis of the invention product, a few data relative to environmental pollutants as PCBs, PCDDs, PCDFs and benzo[a]pyrene, of which we will discuss in details later on, are also reported. Without getting into the merits of the presented data, we emphasize anyway that neither in any point of the Description it is stated that the presented method is able to lower the content of said substances, nor the same matter is in any manner claimed. It is then thought that such data are quite occasional, and above all the low content of pollutants to be simply a consequence of their reduced content in the starting oil, either because derived from low polluted seas, or simpler because of previous purification of the oil itself in the state of triglyceride: it is in fact known that a few environmental pollutants are lower boiling in comparison to triglycerides and are then removable by molecular distillation.

We have also noticed several citations of bibliographic references dealing with the usual urea treatments—already above mentioned—which are performed to concentrate omega-3 acids, such as U.S. Pat. No. 5,679,809, EP 0347509, and others (par. [0053]), but as we will see, no one of these methods in consideration of the different procedure and purpose with respect to the present application seems to constitute a valid prior art towards the present application, and not even has addressed the Authors themselves of the here discussed application US 20120053242 to the use of urea.

The U.S. Pat. No. 5,679,809 reports that the ethyl esters of fatty acids are treated with urea in ethanol, and that by cooling, a solid phase containing the insoluble inclusion complexes separates from a liquid phase containing a fraction enriched of ethyl esters of PUFAs.

The application EP 0347509 describes that a mixture of fatty acids is subjected to complexation with urea to remove the saturated acids and most of monounsaturated acids, and then the filtrate is submitted to fractional crystallization at low temperature. Impurities by far the most damaging, however, are those entirely foreign to the natural oily material and deriving from environmental pollutants, many of which are particularly fat-soluble and tend to concentrate together with the various fat components (POPs, Persistent Organic Pollutants). The main features of these substances are the persistence over time, the bioaccumulation through the food chain, the potential for dissemination and long-range environmental transport, and their toxicity. Many of these substances are clearly teratogenic, mutagenic and carcinogenic. After a long preparatory phase, the first official act against these substances derived from Stockholm Convention on POPs held on 22-23 May 2001 in Sweden, which identified 12 distinct chemical classes (the "dirty dozen") as the most aggressive and dangerous to the human health and the environment, including agriculture and cattle breeding. Many of these substances were in the past, and some are even currently used as pesticides (herbicides, insecticides, fungicides, rodenticides, etc.). The conclusion of the Convention was to ban the production and use of many of these substances, including other industrial uses, to limit the use of DDT in malaria control only, and to limit the unwitting and unintentional production of other substances such as "dioxins" and "furans", unwanted by-products of a series of chemical processes and/or combustion, and as "PCBs", whose industrial use remains anyway prohibited.

The objective of defining and controlling additional Persistent Organic Pollutants was then pursued in subsequent years by various POPs Review Committees, as well as by various Regional Agencies for the Environmental Protection, as the Italian ARPA. To confirm this, numerous studies report the accumulation of often relatively high concentrations of environmental pollutants such as dioxins, PCBs, brominated flame retardants, but also of DDT and its metabolites, and pesticides such as toxafenes and others, in marine organisms and vegetable environments, and therefore in the oils of marine origin and from vegetable seeds. The danger posed by these substances to humans and animals have caused a growing concern for the content of toxic substances in food and the food chain. Food products that do not contain, or have limited content of pollutants, are gaining increased popularity and market capacity. Therefore the elimination or reduction of pollutants in food products has great potential to substantially increase their ability to sell and their value added, with particular reference to their request in the "baby foods industry" and "infant formulas". Particularly required by the market are polyunsaturated acids, such as EPA and DHA, as well as new technologies for their purification as these substances are particularly sensitive to heating at high temperatures, and therefore to distillation, or molecular or short path distillation, which currently represents in fact the more usual method for the purification from environmental pollutants.

In relation to this difficulty represented by the heat sensitivity of the oils containing polyunsaturated and to the more usual methods, reference is made to U.S. Pat. No. 7,732,488 (WO04/007654) and the references cited therein. U.S. Pat. No. 7,732,488 describes a process for decreasing the amount of environmental pollutants in a mixture of oils or fats, according to which it is added to the mixture a low-boiling "working" fluid, by then submitting the mixture to at least a phase of "stripping", during which a part of the environmental pollutant is distilled off along with the volatile "working" fluid. This method seems to be ameliorative, but not decisive with respect to the previous art, as it is also limited to the purification of oils (triglycerides), in that only the oils are high-boiling enough not to co-distill in the phase of stripping; as the working fluid is defined as "low-boiling", but it is also represented by ethyl esters or fatty acids or the like, such as to require a temperature of 180-200° C. for an efficient phase of stripping; and finally it seems on the average more suitable to a reduction of pollutants than to their total elimination, involving anyway long heating times, formation of by-products, complex equipments such as molecular distillation, and high costs.

Also the other mentioned methods of the prior art show that the technique of molecular distillation, although of some efficacy, is anyway very limited and does not represent at all a definitive solution of the serious problem of the accumulation of environmental pollutants in oils and fats, which so seriously reduces their value and their use. Since in the human use it is now a rule to isolate and concentrate polyunsaturated fatty acids, or derivatives thereof, considered to be the components of therapeutic and nutritional value, new direct purification methods of the most valuable products for human pharmaceutical use and for nutritional use in animals, including aquaculture, would be highly desirable.

Turning to a more detailed examination of POPs, one of the most common and most toxic classes is that defined by the generic term of dioxins, actually consisting of the two chemical families of polychlorinated dibenzo-para-dioxins (PCDDs) and polychlorinated dibenzo-furans (PCDFs).

Dioxins are not produced intentionally and the source of exposure for humans is mainly that of the environment, through the intake of contaminated foods, particularly animal oils and fats.

There are a total of 75 congeners of dioxins and 135 congeners of furans, which differ in the number and position of the chlorine atoms on the benzene groups, but of these only 7 PCDDs and 10 PCDFs are of particular concern from the toxicological point of view. Generally PCDD/PCDF are not detected as individual compounds, but as mixtures of the latter toxic congeners, having attributed to each of them an appropriate "toxic equivalency factor" (TEF), more precisely the WHO-TEF which is used for food samples (European Commission Regulation (EC) 1881/2006, Off.J.EU, L364/5; 20 Dec. 2006, p. 20).

TEF values were determined experimentally as activation capacity of the receptor Ah (the key step for the next triggering of toxic effects), by measuring the binding affinity of the various chlorinated compounds towards Ah, in comparison to that of 2,3,7,8-tetrachloro-dibenzo-dioxin (2,3,7, 8-TCDD) taken as reference unitary value.

The overall concentration of PCDD/PCDF is therefore expressed as "toxic equivalents" or "equivalent toxicity" (TEQ), and is calculated by summing the TEF values for the individual congeners multiplied by the respective concentrations. The contribution to the sum in TEQ of each congener undetectable is considered equal to the limit of quantification (upper-bound).

The highest WHO PCDD/PCDF TEQ for marine-derived oils intended for human consumption according to the above Regulation (EC) 1881/2006, p. 18, is 2 pg/g oil (Breivik 2007, pages 246-247). According to USP 37, the acceptance criterion corresponds to "no more than" (NMT) 1 pg/g WHO toxic equivalents.

Another group of chemical contaminants is constituted by industrial agents such as polychlorinated biphenyls (PCBs), consisting of variously chlorinated biphenyl molecules. PCBs, before the trade and use were prohibited, were widely used industrial products, used as dielectric fluids, pesticides, flame retardants, paint components and so on. The exposure to humans is due to environmental contamination (landfills, inadequate waste disposal, emissions into the atmosphere from evaporation or fire, etc.).

The polychlorinated biphenyls include a range of 209 congeners, but of these only 12 have similar toxicological properties to "dioxins" and "furans", and are therefore called dioxin-like PCBs (DL-PCBs). Even for DL-PCBs were determined the Toxic Equivalency Factors TEF and their toxic equivalent TEQ is usually given cumulatively with that of dioxins. The maximum level for the sum of dioxins and DL-PCBs (WHO PCDD/PCDF—DL-PCB TEQ), as specified above, is equal to 10.0 pg/g oil.

The sum of other 6 congeners defined "indicators" or "markers" (IUPAC name: PCB 28, 52, 101, 138, 153, 180) is considered by the EFSA (European Food Security Agency) an adequate indicator of the presence of non dioxin-like PCB (NDL-PCBs) and of human exposure to them. This value is expressed in ng/g oil.

According to USP 37, the acceptability of the PCB markers—PCB 118 included—is limited to NMT 0.5 ppm (0.5 micrograms/g).

PBDEs are polybromo-diphenyl ethers, therefore constituted by variously brominated diphenylether molecules, and then with some conceptual analogy with the structure of the PCBs. They comprise a series of 209 congeners, named according to the IUPAC with increasing numbers according to the number of bromine atoms (1 to 10), and some of them are highly neurotoxic and also carcinogenic.

They are used as flame retardants in polyurethane foams, plastic ABS, in polystyrene, and are considered to be "emergent" persistent chemical pollutants. Of certain terms, industrial production has already been banned, but his presence was anyway demonstrated in polluted waters and in landfills, and the sum of PBDEs (DBE-28, 47, 99, 100, 153, 154, and 183) was highlighted up to 3.8 ng/g or more in samples of fish oils (Zennegg M et al, Organohalogen Compounds, 68, 1967, 2006; U.S. Pat. No. 7,732,488).

Polycyclic aromatic hydrocarbons (PAHs) are compounds formed by two or more condensed aromatic rings that results from the incomplete combustion of organic matter, petroleum derivatives or biomass. They are transported by air masses both to the state of gas, or adsorbed on the solid fraction, and are of toxicological interest because they are considered possible carcinogens. PAHs are expressed as the sum of different compounds, depending on the matrix in which are searched, currently expressed as the marker substance benzo[a]pyrene and with a maximum tolerated limit of 2 ng/g in oils and fats (Regulation (EC) 1881/2006, Section 6, p. 18).

The problem of environmental pollution is extremely serious that cannot be exhausted in a single study, but also a single indication in extensive nature can be of immeasurable benefit to human well-being, the animal and the environment world. Among other POPs not discussed here in detail, but still citable by way of example, the following are also mentioned: 2,2 bis- (p-chlorophenyl)-ethane (DDE), 2,2 bis-(p-chlorophenyl)-1,1-dichloroethane (DDD) and 2,2 bis (p-chlorophenyl)-1,1,1-trichloroethane (DDT), the latter tracked anywhere in the global environment, polybrominated-biphenyls (PBBs), hexachlorobenzene, hexachlorocyclohexane isomers, and others. Even heavy metals and organometal compounds represent a serious problem for human health and environment, and in particular methyl-mercury can induce serious cerebral alterations in childhood and neurological damage in the adult, therefore the European legislation has fixed a maximum limit of 0.5 mg/kg in fish products. However, since heavy metals have a greater affinity for proteins than for lipids, the presence of heavy metals in fish oils is not a primary issue (Breivik 2007, page 133).

According to the expert, POPs should be removed, in the greatest possible amount, directly from the starting oils, before starting the concentration processes of polyunsaturated fatty acids, thereby taking advantage of the greater difference in boiling points between the most high-boiling triglycerides and the various POPs, thus making it more effective the distillation/molecular distillation procedures (Breivik 2007, page 133). A further advantage is achieved by the addition of a so-called "working fluid" before distillation (U.S. Pat. No. 7,732,488), as already reported.

Despite this, the presence of many classes and within them of different molecular species of POPs, each with its own chemical-physical features and different boiling points, make this very labor-consuming for losses of time and of yields and increased costs, and generally able to decrease the presence of a pollutant without practically never eliminate it in its entirety, and in the case favorable for a single product without being able to extend the purification to the totality of POPs.

Other methods of partial utility for the reduction of POPs, but never to cancel their presence, include the treatment with active carbon and/or the deodorizing process with significantly increased times and temperatures, and with the relative problems, without being competitive with the distillation (Breivik 2007, page 133). Even chromatographic processes can have some efficacy on a single compound, never on the totality of POPs which are generally dispersed throughout the whole chromatographic picture.

We have therefore concluded that none of the current techniques is capable of purifying the compositions in question from all the impurities described above, and only if used in combination, repeatedly and with serious losses of yield can approach the limits imposed by the various laws, without ever achieve a substantial absence of each pollutant, as it would be desirable.

For example, the molecular distillation is certainly capable of removing the high-boiling fractions with the greater part of the more polar impurities, as the oligomers and certain other products of oxidation, even with severe yield losses, but is not able to eliminate totally the above pollutants polychlorinated, that in dependence on the degree of substitution have a wide range of distillation temperatures.

Likewise, the use of supercritical fluids can lead to remove polar substances by means of the extraction of fatty acids, but these will always be accompanied by the lipophilic polluting substances, equally extractable from the supercritical solvent. It is thought that other technologies for the systematic elimination of POPs are not available. In particular the use of urea is presented in the literature only as being eligible for inclusion, and then isolation and elimination of saturated and monounsaturated fatty acids, and therefore to the concentration of the polyunsaturated acids, which however would be accompanied so at an increased concentration of the extraneous impurities. The inclusion of polyunsaturated components appears from the literature of difficulty increasing with the increase of their concentration and their relative degree of unsaturation.

None of the known technologies, as far as we know, can also lead to polyunsaturated compositions substantially free from all the above mentioned "furan" components, phytanic and pristanic acids or derivatives thereof, branched long chain hydrocarbons such as squalene, large part of the polymers of polyunsaturated acids, and the essential totality of POPs, in the more particular case in a single step.

SUMMARY OF THE INVENTION

We have vice versa identified a new and surprising purification technology, which essentially consists in extracting from a composition comprising long chain polyunsaturated fatty acids, of animal and/or vegetable origin, already brought to the desired concentration and ratio of the components (or from a solution thereof), no by-products and pollutants, but directly and selectively all desired polyunsaturated components, so isolating in the exhausted mother solution all the polluting material. It thus adopts, unlike the prior art, only a specific and selective method for the desired polyunsaturated components, instead of using the different extraction methods relating to the different chemical-physical properties of the various discussed pollutant families.

In a first aspect, therefore, the present invention relates to a composition comprising long chain polyunsaturated fatty acids of animal and/or vegetable origin, belonging to the omega-3 and/or omega-6 series, having 2-6 double bonds and 18 or more carbon atoms, or their salts or esters, said composition being substantially free of furan fatty acids or salts or esters thereof, wherein said furan fatty acids or their corresponding salts or esters are in a total concentration not higher than 0.1%, i.e. not higher than 1000 ppm, and preferably not higher than 0.01%, i.e. not higher than 100 ppm.

In particular said esters can be alkyl esters, preferably C1-C3, or glyceryl mono-esters and/or di-esters and/or tri-esters.

In a second aspect, the present invention relates to a method for the preparation of a composition as defined above, wherein said esters are alkyl esters, preferably C1-C3, comprising the steps of:

a) subjecting an oil or fat of animal or vegetable origin, including the marine, aquaculture, algal or fermentative origin, comprising at least one acyl group with at least 18 carbon atoms, with 2-6 double bonds of the omega-3 and/or omega-6 series, to alkaline or acid hydrolysis or to transesterification with aliphatic alcohols, preferably C1-C3, optionally under enzymatic catalysis;

b) subjecting the product of the above hydrolysis or transesterification to a purification process by means of total inclusion into urea, to obtain an inclusion complex, which is isolated and washed;

c) obtaining the above composition by dissolution in water of such inclusion complex and separation of the oily phase formed following said dissolution or by extraction of said oil phase with an organic solvent immiscible with water, typically hexane, followed by evaporation of said solvent to dryness, or by direct extraction from the inclusion complex by means of fluids in the supercritical state, in particular carbon dioxide.

In a further aspect, the present invention relates to a method for the purification of a composition comprising long chain polyunsaturated fatty acids of animal and/or vegetable origin, belonging to the omega-3 and/or omega-6 series and having 2-6 double bonds and 18 or more carbon atoms, or their salts or alkyl esters, preferably C1-C3, the method comprising the steps of:

a) treating 1 part by weight of the above composition with at least 3 parts by weight of urea in a polar solvent, preferably a protic solvent such as a lower alcohol, as methanol or ethanol, optionally containing up to 20% of water, at the boiling temperature, to form a urea inclusion complex containing the above composition;

b) cooling to precipitate such urea complex and isolating it by filtration or centrifugation;

c) obtaining a purified composition by dissolution in water of such urea inclusion complex, and separation of the oily phase formed following said dissolution or by extraction of said oily phase with an organic solvent immiscible with water, typically hexane or the like followed by evaporation of said solvent to dryness, or by direct extraction from the inclusion urea complex by means of supercritical fluids, particularly carbon dioxide.

A purified particularly preferred composition according to the invention envisages that fatty acids have marine origin and are derived in particular from fish oils, including fish from aquaculture, or "krill oils", or from algae and other oleaginous microorganisms, or from "single cell fermentation" starting from selected strains of algae or other microorganisms, and include eicosapentaenoic acid (EPA, C20: 5 n-3, all cis) and/or docosahexaenoic acid (DHA, C22: 6 n-3, all cis), or a salt thereof or alkyl ester, preferably C1-C3.

Conveniently, in the above preferred purified composition, the alkyl esters are ethyl esters, and the concentration of EPA or EPA ethyl ester, or DHA or DHA ethyl ester, or their sum, is between 15 and 100%, preferably between 50 and 100%, of the composition weight.

As a further aspect of the invention, said purified compositions can be used for the synthesis of new lipid derivatives, both by chemical and enzymatic route: among these in particular the already mentioned glyceryl mono-esters and/or di-esters and/or tri-esters of EPA and/or DHA, that they too will be comprised between 15 and 100%, preferably between 50 and 100% by weight of the composition.

The invention also relates to the use of the above-mentioned, preferred purified composition for the preparation of formulations useful as food ingredients, food and dietary supplements, foods for special medical purposes (functional foods), foods for animal use and aquaculture, food formulations for the infancy, cosmetic and pharmaceutical preparations, by virtue of their high content of long chain fatty acids or their derivatives, having polyunsaturated character or specifically belonging to the omega-3 series, or for the preparation by chemical route of other derivatives, such as e.g. the corresponding mono-, di-, or triglycerides.

In a further aspect, the present invention refers to the above purified composition for its use in the prevention and treatment of risk factors for cardiac, cardiovascular and cardio-circulatory diseases such as hypertension, coagulation disorders and platelet aggregation, the severe and moderate hypertriglyceridemia (resp.>500 mg/dl and >200 mg/dl), and hypercholesterolemia, in particular familial and genetic forms, also in association with other drugs and in particular with statins, in the prevention and treatment of cardiac, cardiovascular and cardio-circulatory diseases, such as coronary-atherosclerotic illnesses, and cardiac and cerebral ischemic states, including myocardial and cerebral infarction, and the reduction of the risk of sudden cardiac death resulting from myocardial infarction; those due to electrical causes and involving the onset and propagation of cardiac rhythm, including arrhythmia and atrial and/or ventricular fibrillation; and those due to mechanical defects of the cardiac pump, such as the heart insufficiency and decompensation, and/or the congestive "heart failure"; further, for use in the prevention and treatment of central nervous system (CNS) disorders, including the epilepsy, the various forms of depression, bipolar disorders, pediatric disorders from attention defects and hyperactivity disorder (ADHD), learning and memory defects, various forms of schizophrenia, Alzheimer's disease and various forms of dementia; and finally for use in the prevention and treatment of retinopathy and dry eye symptoms, metabolic syndrome, defects of metabolism and related to obesity, type 2 diabetes, liver disorders, diseases of the connective tissue and joints, of inflammation, autoimmune diseases, ulcerative colitis, psoriasis and tumor disease.

Advantageous processing and development of the present invention are deductible from the dependent claims below.

DETAILED DESCRIPTION

Figure 1:
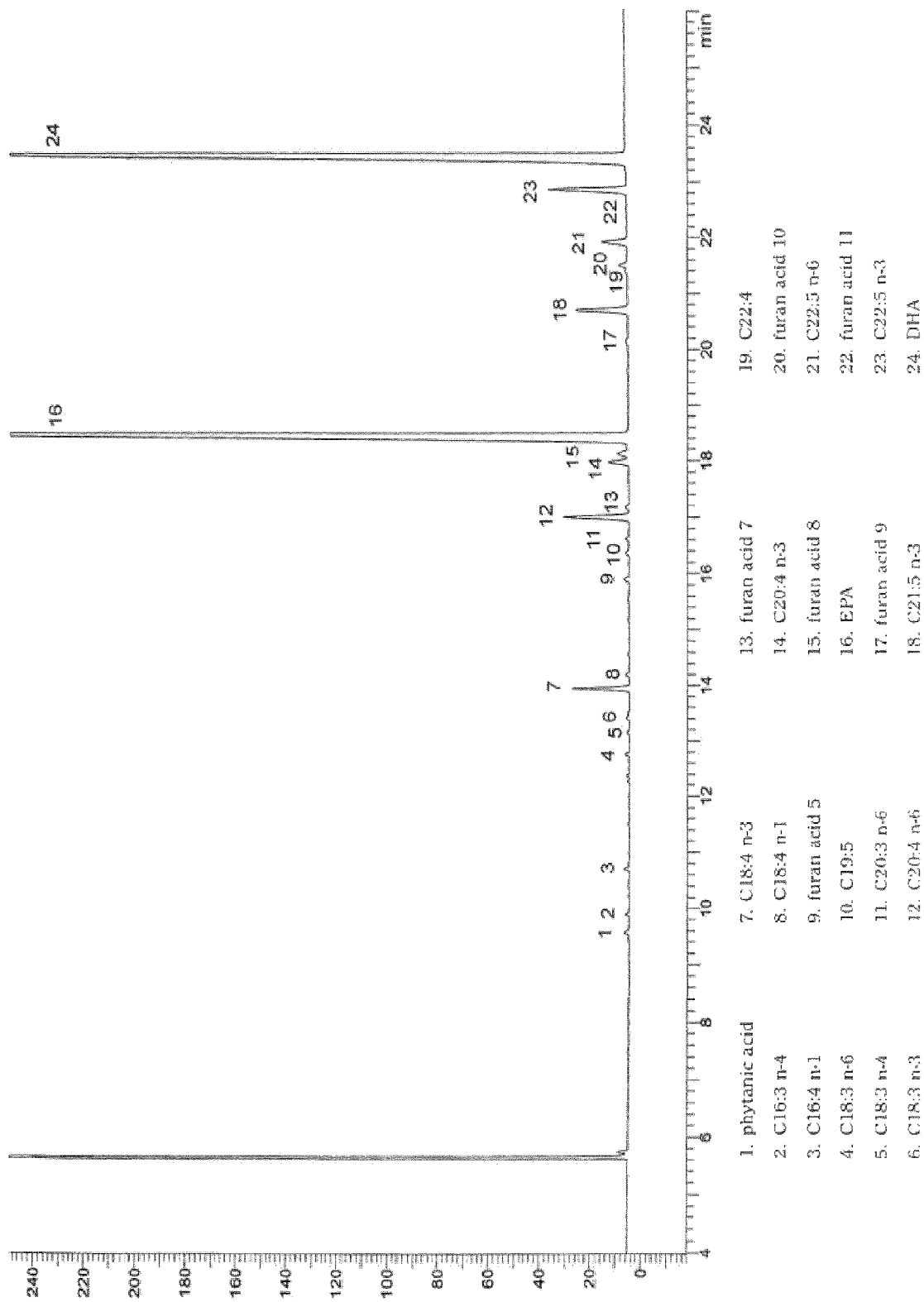
FIG. 1 shows a gas chromatography analysis of PUFA.

In the present description the salts of the polyunsaturated acids are represented by salts with alkali metals, e.g. sodium and potassium, alkaline earth metals, e.g. calcium, with basic amino-acids such as lysine and arginine, with meglumine, choline and mono-, di-, and tri-ethanolamine, and the like, if pharmacologically acceptable.

The alkyl esters are represented by esters with aliphatic alcohols, even at very long chain as found in the natural "wax", but are preferably represented by esters with lower alcohols C1-C3.

It is also obvious that these purified compositions can be then modified chemically or enzymatically to provide purified compositions of other derivatives, as e.g. the corresponding mono-, di-, and triglycerides.

These glycerides are also reported as monoacyl-glycerols (e.g. omega-3 monoacyl glycerol) in position sn-1 or sn-2, or as diacyl-glycerols in position sn-1,2 or sn-1,3, or again as triacyl-glycerols.

The enzymatic production of these acyl glycerols through specific lipases, is dictated by precise experimental conditions according to the literature, and it is well summarized e.g. from "Breivik 2007", pp. 157-159.

This our method is based essentially on the inclusion of polyunsaturated substances in a quantity of urea in excess in respect of literature requirements.

We have confirmed that the process of inclusion is actually preferential for saturated and monounsaturated components, when these are prevalent in the composition, as occurs in natural products not yet subjected to the processes of concentration of polyunsaturated substances, but it is however also possible complexing the totality of the polyunsaturated components when urea is used in excess, and that this ultimately is just as easy when the saturated and monounsaturated components are relatively scarce in the composition and nearly or entirely absent: if essentially absent, we have found that an excess of urea is not even necessary and that a total complexation is also easily obtainable in one single step, which is altogether surprising. In these cases, the process takes place smoothly in respect of both medium and long chain fatty acids, or salts or esters thereof, such as LA, ALA, ARA and the others cited above, and as EPA and DHA. As we have also found, it then also permit an easy recovery of all these products from the formed urea complex, through standard procedures of the literature.

The aspect, however, more surprising of the new procedure is that substantially all of the impurities, by-products and pollutants described above, can be eliminated in one operational step, remaining non-complexed in the solvent phase: we include in this statement almost all the substances not structurally similar to fatty acids, esters and most simple derivatives thereof, substances which we define here as structurally "bulky" compounds, e.g. most of those containing a chain branching in the fatty acid or an organic ring and polycyclic compounds, condensed or not, saturated or unsaturated, as in any case we will report hereinafter or individually or divided by classes.

The purification process thus extends substantially the totality of the pollutants described above, and includes e.g. all acids furan, long-chain branched fatty acids and hydrocarbons, as well as dioxins and furans, polychlorinated biphenyls, polybrominated diphenyl-ethers, cyclic and polycyclic hydrocarbons, simple and condensed, and other POPs.

It remains also understood that in this purification process, each of the aforementioned substances comprised in each concentration interval, and their sum within the same intervals, will be at least 5 times reduced (reduction of at least 80%), or preferably at least 10 times reduced (reduction of at least 90%) compared to the compositions from which they originate, or still in the great majority of cases they will be "essentially zero" or "zero." A content defined as "essentially zero" indicates a concentration below the limit of detection (LOD), but as a precaution identified with the limit of quantification (LOQ), while it is defined as "zero" if the value less than the LOD is identified as zero.

The degree of elimination of all these unwanted substances is evidently obtained also by means of the careful washing of the urea complexes for the removal of the mother liquors and of their polluting load, as recommended by the procedure, but never sufficiently highlighted by the known literature, for the evident fear of considerable yield losses due to partial re-dissolution of the complexes by the washing solvent.

Details of intervals and maximum levels obtainable with the invention process will be given below.

Some or most of the oligomers and polymers, of peroxy-derivatives, metal ions and metallo-organic compounds, and some sterol substances, will also be reduced.

An important consideration is that the purification process of the invention does not require to be modified according to the content of pollutants and by-products present in the starting material, and to be eliminated, as e.g. prolonging the times or modifying the "stripping" temperatures in the distillation according to the prior art, or the number or the size of the fractions to be discarded in case of purification by chromatography with supercritical fluids.

With the new process, it will instead use just as well any material, also heavily polluted, as e.g. oil from fish caught in polluted seas, very rich therefore in POPs, and as such rejected by the market or sold at bargain prices; or fish oil-fed waste food rich in phytanic acid, or vegetable oils from highly polluted sites.

In conclusion, according to a first aspect of the purification method according to the invention, a composition low in polyunsaturated acids or salts or esters thereof, that is with a content equal to 15-30%, can be subjected to treatment with 3-6 total parts by weight of urea in 3 consecutive steps, first obtaining a complex mainly with saturated or monounsaturated acids, and then progressively with polyunsaturated acids, then the complexes are combined and acids are recovered to obtain a composition with the same low initial content of polyunsaturated acids, if this is desired, but substantially free of all the above mentioned impurities, removed with the final mother liquors of the complexation process. This procedure is well suited for obtaining purified compositions in a similar concentration of polyunsaturated components—or slightly increased—compared to that of natural products, which we denote as indicatively greater than 15% in many seed oils, or around 20-30%, typically 18% EPA+12% DHA as is the case e.g. in many fish oils.

According to a second aspect of the purification method according to the invention, a composition with a medium content of polyunsaturated acids or salts or esters thereof, that is with a content equal to 31-80%, can be subjected to treatment with 3-5 total parts by weight of urea in two successive steps.

In this second aspect of the invention, such compositions at medium concentration, to be used in the purification step, can be obtained with all the concentration methods reported in the literature and we mentioned above, starting from low concentration compositions.

Among these methods, particularly advantageous is to use just the complexation technology with urea, to be used in 0.1 parts by weight up to a maximum dose of 3 parts by weight, usually 1-2 parts by weight, relative to the starting material, by varying this quantity in dependence upon the desired degree of concentration.

Isolated and eliminated the first complex obtained, rich in saturated and less polyunsaturated acids, it is then possible to continue with the purification step by directly using the mother liquors of the concentration, without prior isolation of the concentrated polyunsaturated acids.

This procedure allows to obtain easily purified compositions at medium concentration of polyunsaturated acids, such as e.g. 50-60% by weight or more in accordance with the 2063 monograph of E.P. 5.0, but also in the range of 30-80% by weight, preferably 50-80% by weight, depending on the type and the number of treatments of the concentration step.

According to a third aspect of the purification method according to the invention, a composition with a high content of polyunsaturated acids or salts or esters thereof, that is with a greater than 80% content, can be subjected to treatment with 3-4 total parts, preferably 4 parts by weight of urea in one single step.

An advantageous variant of the process is to perform the purification by complexing with urea immediately before the final distillation, or extraction with supercritical fluids, if desired, what allows the total elimination of the residual organic solvents of the reaction that may be present.

The procedure thus led permits to easily obtain purified compositions in concentration e.g. greater than 80% by weight of polyunsaturated components EPA and/or DHA, and greater than 90% by weight of total omega-3, such as those required by the EP monograph 1250, or in the range of 80-100% by weight of EPA and/or DHA.

To complete the overall description of the process of the invention for the preparation of compositions of highly purified polyunsaturated acids, starting from natural compositions of oils and fats and including other treatment steps already known, the procedure may be explained briefly as follows:

- an appropriate oil or fat of animal or vegetable origin, including the marine origin, from aquaculture, algal or fermentation origin, and comprising at least one acyl group having 2-6 double bonds of the omega-3 and/or omega-6 series and 18 or more carbon atoms, is subjected to alkaline or acid hydrolysis or transesterification with aliphatic alcohols, preferably C1-C3, according to standard procedures known to the expert;
- if desired, the product is subjected to the optional process of concentration of the polyunsaturated components by distillation, molecular or "short path" distillation, fractionation with progressive complexation with urea of saturated or monounsaturated (or generally less unsaturated) components followed by elimination of the complexes, counter-current extraction, extraction with aqueous silver nitrate, extraction and/or fractionation with supercritical fluids, chromatographic procedures, all in accordance with standard procedures known to the expert and continuing up to the desired degree of enrichment and ratio variation of components of the final composition, including also the isolation of compositions containing essentially only EPA or DHA alone;
- as essential purification step according to the invention, the crude composition obtained as above and optionally concentrated in polyunsaturated components, is subjected to the purification process by means of essentially total inclusion into urea, followed by isolation and thorough washing of the inclusion complex obtained, its eventual dissolution in water and subsequent recovery of the purified polyunsaturated components by solvent extraction (or with supercritical fluids) of the composition and subsequent evaporation to dryness;
- if desired, the final recovery of the purified composition is carried out by molecular/short path distillation or extraction with supercritical fluids, according to standard procedures known to the expert.

Optionally the purified composition can be subjected to further proceedings of concentration or adjustment of the component ratios, or it can be modified by chemical means to include other derivatives, as e.g. the corresponding mono-, di-, or triglycerides, in the purified state, which fall then they also in the spirit of the present invention.

Still optionally the mother solution of the purification step, after filtration of the lipid inclusion complex, can be concentrated to dryness leading to a composition enriched in furan acids, phytanic acid, pristanic acid, or salts or alkyl esters thereof, and squalene, useful for the isolation of said compounds by known techniques, such as molecular distillation and/or chromatography processes with organic solvents or other fluids in the supercritical state, such as carbon dioxide.

The execution of the new complexation procedure differs from that of the literature only as it is additional and carried out for a different purpose, but is not substantially different in the procedure. It still uses preferably e.g. a solution of polyunsaturated fatty acids in methanol or ethanol, partially aqueous ethanol (containing up to 20% of water) or other equivalent polar solvents, as reported by Schlenk H and by Swern D, before mentioned. The amount of solvent used in the process is usually of 4,5-7 parts by weight of methanol, or of 45-65 parts by weight of ethanol, then it is added with at least 3 parts by weight of urea, heated briefly to the boiling point and complete solution. It is then cooled to around 0° C. (range+25/−20° C., as usual), obtaining precipitation of the urea complex of the desired polyunsaturated acids, and then discarding the solution containing all the polluting substances, as described above: it is well clear that the new procedure uses the urea complex and eliminates the mother liquor, just the opposite of what happens in the process of literature.

This phase of treatment with urea is preferably performed as follows:

- if the composition has a content of the aforementioned polyunsaturated fatty acids or their salts or alkyl esters comprised between 15 and 30%, one part by weight of the composition is treated with 3-6 parts by total weight of urea in three successive steps;

if the composition has a content of the aforementioned polyunsaturated fatty acids or salts or alkyl esters thereof between 31 and 80%, one part by weight of the composition is treated with 3-5 parts by total weight of urea in two subsequent steps;

if the composition has a content of the aforementioned polyunsaturated fatty acids or salts or alkyl esters thereof higher than 80%, one part by weight of the composition is treated with 3-4 parts, preferably 4 parts, by weight of urea in one step.

A useful variation is to concentrate the mother solution before eliminating it, e.g. up to half the volume, in order to recover a second aliquot of urea inclusion complex and to improve the yield of the process.

The precipitated solid is carefully washed with methanol or ethanol, possibly saturated with urea and cooled to minimize losses, it is then dissolved in water and the purified composition is separated as the oil phase or is extracted with organic solvent water immiscible, as e.g. with hexane or the like. After evaporation of the solvent, as is well known to the expert of the sector, and any other literature treatments, as e.g. molecular distillation, the required polyunsaturated acids in highly purified form are so obtained.

As an alternative, the purified composition is extracted directly from the washed solid complex with supercritical fluids, in particular CO2.

An aspect of particular importance with respect to known methods relates to the amount of urea, that in said known processes is carefully limited to avoid any losses of polyunsaturated components, while according to the invention must be in excess appropriate for a quantitative recovery of all the material. The quantity will depend of course on the composition of the material to be purified, but generally consists of 3 to 4 or 5 parts by weight, or more. It is noteworthy, however, that said excess will decrease in the case of the concentrated polyunsaturated compounds, being lower the competitive complexation of saturated or monounsaturated compounds, and 3 parts by weight or so of urea will usually be sufficient.

With the use of the invention, we treated and purified each type of composition based on polyunsaturated fatty acids, and any concentration, even if the treatment will be more and more important in the concrete with the increase of their concentration to the detriment of other saturated and monounsaturated components. Further, the composition will be of greater interest for the human consumption or even for the pharmaceutical use, but is also evident that it is not even permitted to recycle as food in animal, e.g. aquaculture, the by-products and pollutants (POPs) already present in foods and in not yet purified compositions.

Some compositions treated according to the new process are reported here in greater detail as not limiting examples:

a) compositions comprising long chain polyunsaturated fatty acids of animal and/or vegetable origin, or their salts or alkyl esters, e.g. of marine origin and obtained starting from fish oils or krill oils, or oils from aquaculture fish, or still from algae or other oleaginous microorganisms, or "single cell fermentation" from selected strains of algae or other microorganisms, including the recombinant ones, or e.g. deriving from seed oils or other oils and fats of vegetable origin, and wherein the compositions have essentially the same concentration of polyunsaturated components as in oils and fats of animal/plant origin from which they are derived, generally greater than 15-20%.

b) Compositions of fatty acids omega-3 and/or omega-6, comprising e.g. eicosapentaenoic acid (EPA, C20: 5 n-3, all cis) and/or docosahexaenoic acid (DHA, C22: 6 n-3, all cis), or a salt or alkyl ester, preferably C1-C3, of any origin and in any ratio between them, and at a concentration higher than 15%, or an average concentration of generally 20-50%, or a particularly high concentration of 50-100%.

c) Compositions of "omega-3-acid ethyl esters 60" as essentially described in the monograph no. 2063 of the European Pharmacopoeia (EP 5.0), typically containing a minimum of 50% EPA ethyl ester (min 25-40%) plus DHA ethyl ester (min 20-40%), and a minimum of 55%, 60% or 65% ethyl esters of total omega-3 acids.

d) Compositions comprising long chain polyunsaturated fatty acids, or salts or alkyl esters thereof, in which the concentration of EPA ethyl ester or DHA ethyl ester, or of their sum, is between 50% and 100% of the composition.

e) Compositions of "omega-3 acid ethyl esters 90" as essentially described in the monograph no. 1250 of E.P. suppl.2000 and subsequent, typically containing a minimum of 80% of EPA ethyl ester and DHA ethyl ester, of which a minimum of 40% of EPA ethyl ester and a minimum of 34% of DHA ethyl ester, and a minimum of 90% of ethyl esters of total omega-3 acids.

f) Compositions as essentially described in the monograph "Omega-3-Acid Ethyl Esters" of USP 37, typically containing not less than (NLT) 800 mg/g and not more than (NMT) 880 mg/g of EPA ethyl ester (EPAee) and DHA ethyl ester (DHAee), NLT 430 mg/g and NMT 495 mg/g of EPAee, NLT 347 mg/g and NMT 403 mg/g of DHAee, and NLT 90% by weight of the total of ethyl esters of omega-3 acids.

g) Compositions of fatty acids essentially as described in patent IT 1235879, typically containing at least 80% by weight of omega-3 polyunsaturated fatty acids, among them EPA and DHA are present in a ratio of 1:2 to 2:1 and account for at least 75% by weight of total fatty acids and other omega-3 acids C20, C21 and C22 constitute at least 3% by weight, and wherein said acids can all be present in the form of salts or derivatives pharmaceutically acceptable.

h) Compositions comprising long chain polyunsaturated fatty acids, or salts or alkyl esters thereof, in which the concentration of EPA ethyl ester or DHA ethyl ester, is greater than or equal to 80%, preferably greater than or equal to 90%, or the sum of their concentrations is between 50% and 100% of the composition.

As already mentioned before, it remains, however, understood that all the compositions, after purification according to the method of the invention, lead to corresponding compositions having concentrations of polyunsaturated components essentially the same, except for the appropriate obvious corrections on the rise due to impurities completely removed through the process and already repeatedly cited and described: the entire class of the numerous furan fatty acids, phytanic and pristanic acids, or salts or alkyl esters thereof, squalene, as well as the many pesticides and environmental pollutants (POPs), ubiquitously distributed throughout the animal and plant world.

It is also understood that the concentrations of the polyunsaturated components in all the purified compositions, and as such susceptible to the most varied uses in animals and especially humans, e.g. such as food supplements, foods for medical use, drugs, etc., will be expressed as concentrations "by weight" with respect to the total weight of the composition. The contemplated method is that of the gas chromatography GC, but the analysis will be conducted in comparison with the pure substances at 100% and determining the necessary GC response factors. It is well known that the concentration simply deducted through the ratios of chromatographic areas, as is often carried out on the low-purity compositions, can lead to extremely serious evaluation errors because obviously many impurities are retained in the gas chromatographic column and are not revealed by the detector of the instrument, thus decreasing the sample total GC area and therefore leading to an overestimation of the polyunsaturated components e.g. as EPA and DHA.

After purification in accordance with the process of the invention, numerous purified compositions of polyunsaturated fatty acids were obtained, of which some examples of course not limitative are briefly and in general terms reported here below:

1) Compositions which comprise long chain polyunsaturated fatty acids of animal and/or vegetable origin, belonging to the omega-3 and/or omega-6 series, having 2-6 double bonds and 18 or more carbon atoms, or salts or esters thereof.

2) Compositions as defined in 1), wherein the fatty acids have marine origin and are derived in particular from fish oils or "krill oils", or are derived from fish oils from aquaculture, or still from algae and other oleaginous microorganisms, or "single cell fermentation" from selected strains of algae and other microorganisms, including the recombinant ones, and include eicosapentaenoic acid (EPA, C20: 5 n-3, all cis) and/or docosahexaenoic acid (DHA, C22: 6 n-3, all cis), or a salt or ester thereof, in any ratio.

3) Compositions as defined in 2), wherein the esters are alkyl esters, preferably C1-C3.

4) Compositions as defined in 2) wherein the esters are glyceric mono-esters and/or di-esters and/or tri-esters.

5) Compositions as defined in 3), in which the alkyl esters are ethyl esters, and the concentration of EPA or EPA ethyl ester, or DHA or DHA ethyl ester, or the sum of their concentrations, are comprised between 15 and 100% of the weight of the composition, preferably between 50 and 100% by weight.

6) Compositions as defined in 5), in which the sum of the concentrations of EPA ethyl ester and DHA ethyl ester is higher than or equal to 80% by weight, preferably higher than or equal to 84% by weight, being EPA ethyl ester higher than or equal to 40% by weight, DHA ethyl ester higher than or equal to 34% by weight and the sum of all omega-3 ethyl esters higher than or equal to 90% by weight.

7) Compositions as defined in 5), in which the sum of the concentrations of EPA ethyl ester and DHA ethyl ester is between 80% and 88% by weight, EPA ethyl ester being comprised between 43% and 49.5% by weight, DHA ethyl ester between 34.7% and 40.3% by weight, and the sum of the ethyl esters of total omega-3 acids higher than or equal to 90% by weight.

8) Compositions as defined in 5), in which the concentration of EPA ethyl ester, or DHA ethyl ester is greater than or equal to 80%, preferably greater than or equal to 90% by weight. 9) Compositions as defined in 4), in which the concentration of EPA or DHA or their sum, are between 15 and 100%, preferably between 50 and 100%, of the composition weight.

All these compositions are particularly characterized by comprising:

a sum of furan fatty acids or their corresponding salts or alkyl esters, preferably C1-C3, at a total concentration of less than or equal to 0.1%, i.e. less than or equal to 1000 ppm, and preferably less than or equal to 0.01%, i.e. less than or equal to 100 ppm.

Said compositions are also generally characterized by comprising:

phytanic acid and/or pristanic acid, or their corresponding salts or alkyl esters, at a total concentration of less than or equal to 0.01%, i.e. less than or equal to 100 ppm and preferably less than or equal to 0.001%, i.e. less than or equal to 10 ppm;

squalene in concentrations of less than or equal to 0.01%, i.e. less than or equal to 100 ppm and preferably less than or equal to 0.001%, i.e. less than or equal to 10 ppm;

oligomers of the acids, or salts or esters, in concentrations of less than or equal to 1.0%;

polychlorinated dibenzo-p-dioxins (PCDDs) and polychlorinated dibenzo-furans (PCDFs) in overall concentration of less than or equal to 1.0 pg/g, preferably less than or equal to 0.1 pg/g, value determined in accordance with the toxic equivalency factors (TEFS) of WHO and expressed as toxic equivalents (TEQs);

PCDDs, PCDFs and polychlorinated biphenyls (PCBs) dioxin-like (DL-PCBs) in overall concentration of less than or equal to 5.0 pg/g, preferably less than or equal to 0.5 pg/g, value determined as defined above (TEQs);

PCBs marker in overall concentration of less than or equal to 5.0 ng/g, preferably less than or equal to 0.5 ng/g;

polybrominated-diphenyl ethers (PBDEs) in overall concentration of less than or equal to 5.0 ng/g, preferably less than or equal to 0.5 ng/g;

a sum of polycyclic aromatic hydrocarbons (PAHs), expressed as the marker substance benzo[a]pyrene, less than or equal to 1.0 ng/g, preferably less than or equal to 0.1 ng/g;

other environmental "persistent organic pollutants" (POPs) comprising 2,2 bis-(p-dichlorophenyl)-ethane (DDE), and/or 2,2 bis-(p-dichlorophenyl)-1,1-dichloroethane (DDD), and/or 2,2 bis (p-dichlorophenyl)-1,1,1-trichloroethane (DDT) in overall concentration of less than or equal to 2.0 ng/g, preferably less than or equal to 0.2 ng/g, polybrominaned-biphenyls (PBB) in overall concentration of less than or equal to 5.0 ng/g, preferably less than or equal to 0.5 ng/g; hexachlorobenzene at a concentration of less than or equal to 0.1 ng g, preferably less than or equal to 0.01 ng/g, and hexachlorocyclohexane isomers in overall concentration of less than or equal to 0.1 ng/g, preferably less than or equal to 0.01 ng/g.

While in the purification process it is found that the oligomers are simply reduced compared to the content in the starting materials, being in any case in the lower part of the range described, each of the other substances included in these concentration ranges and their sum within the same intervals, it is at least 5 times reduced, or preferably at least 10 times reduced compared to their content in the not purified compositions from which they originate, or in the great majority of cases is "essentially zero" or "zero".

All purified compositions described in detail above, can then be formulated, either as such or added with suitable diluents, excipients, suspending agents, etc., and/or with suitable preservatives, antioxidants, etc., according to all technologies known in the art, to give all formulations known in the art to allow their use in all the proposed indications. Said formulations comprise, in addition to their direct inclusion e.g. in various foods, or in the form of micro- or nano-encapsulated products obtained according to the prior art, also the formulations for oral use—as drops, soft gelatin capsules, hard gelatin self-sealants capsules, tablets, if required after adsorption on solid support or as inclusion complex, if necessary also in gastro-resistant formulation, etc.—as known in the art, or for topical use—such as creams, ointments, etc.—as well known in the art, or again for the injective administration—such as vials for intramuscular use, slow intravenous drip infusion, etc., after sterilization and/or if necessary after chemical and/or physical modification, e.g. as the glycerides in emulsion, as well known in the art.

With reference to their use, these purified compositions and their formulations will be directed to the preparation and use as a food or food ingredient, of any kind and for any purpose, such as food and dietary supplement, food for special medical purposes (functional food), both new and deductible from the use pharmaceutical, food for animal use and for aquaculture, food infant formula, cosmetic and pharmaceutical preparation, all containing or enriched in long-chain fatty acids or their derivatives, having polyunsaturated properties or specifically belonging to the omega-3 series, or their use will be addressed the preparation by chemical or preferably by enzymatic route, by means of appropriate lipases, as described in the literature, of other derivatives such as e.g. the corresponding mono-, di-, or triglycerides, which will result to be equally well purified.

For all uses, but in particular for the pharmaceutical use, the preparation will preferably be concentrated and enriched in polyunsaturated components, in particular in EPA and/or DHA or salt, or ethyl ester thereof.

Of great and increasing importance are the foods for special medical purposes, or functional foods—also including drinks and supplements—which include specific ingredients, such as in particular the omega-3 acids in all their forms, capable of imparting certain specific benefits for the health (fortified foods). These particular benefits will ultimately be deduced from the pharmaceutical use of those specific ingredients, but can also be new. These functional foods are currently known by the English term FOSHU (Foods for Specified Health Use) or the Japanese term Tokuho.

All uses listed below, and in particular pharmaceutical uses, do not appear at all obvious and predictable on the basis of literature, if it is considered that all the purified compositions used are entirely free from furan fatty acids, where different authors attribute just to them the cardio-protective action of fish oils, such as G. Spiteller, Lipids 40, 755, 2005, and others, the anti-inflammatory action, as T. Wakimoto et al, Proc Natl Acad Sci 108, 17533, 2011 and others, and more similar activities.

In particular, the use of the compositions will be directed to the prevention and treatment of risk factors for heart, cardiovascular and cardio-circulatory diseases, such as hypertension, severe and moderate hypertriglyceridemia (resp. >500 mg/dl and >200 mg/dl) and hypercholesterolemia, in particular the familial and genetic forms, also in combination with other drugs and in particular with statins, and such as the defects of coagulation and platelet aggregation.

A use of great relevance is for the prevention and treatment of cardiac, cardiovascular and cardio-circulatory diseases, such as coronary-atherosclerotic illnesses and cardiac and cerebral ischemic states, including myocardial and cerebral infarction, and reduction of the risk of sudden cardiac death subsequent to myocardial infarction; those of electrical origin and involving the onset and propagation of cardiac rhythm, including arrhythmia and atrial and/or ventricular fibrillation; and those due to mechanical defects of the heart pump as the cardiac insufficiency and decompensation, and/or congestive "heart failure".

In other pharmaceutical uses, the compositions are used for the prevention and treatment of central nervous system (CNS) disorders, including epilepsy, the various forms of depression, bipolar disorder, pediatric pathologies by attention defect and hyperactivity disorders (ADHD), learning and memory defects, various forms of schizophrenia, Alzheimer's disease and other dementias.

Still other pharmaceutical uses include the prevention and treatment of retinopathy and dry eye symptoms, metabolic syndrome, defects of metabolism and correlated with obesity, type 2 diabetes, liver disorders, connective tissue and joint diseases, the inflammation, autoimmune diseases, ulcerative colitis, psoriasis and tumor disease.

EXPERIMENTAL EXAMPLES

The invention will now be illustrated by means of some Examples which will not have, however, any limiting purpose. These Examples are then presented only for illustrative purposes and therefore many other raw materials may be used, as well as many other variations of the process may be carried out and many other compositions of purified PUFAs can be obtained, being however included in the scope of the present invention.

Example 1

The purification was performed on a lot of PUFAs at high concentration, more precisely a lot of ethyl esters of omega-3 acids was used, in accordance with the n.1250 monograph of the European Pharmacopoeia (omega-3-acid ethyl esters 90, batch 201308), also referred to as PUFA_EE or PUFAee, regularly analyzed and approved. The content of EPA ethyl ester and DHA ethyl ester in this lot is relatively high, while the other omega-3 esters are relatively reduced, but overall the composition is within the limits specified in the European Pharmacopoeia. The acidity values, anisidine, peroxides and oligomers are also complying with the requirements of the Pharmacopoeia.

It is obvious that the same purification would also be feasible with a product having e.g. the limits described by the US Pharmacopoeia.

Analytical Method

The percentage content of the various PUFA_EE was determined by GCMS analysis (gas chromatography combined with mass spectrometry). This method allows to change the GC conditions, prolonging the retention times and better separating the individual peaks, without prejudice to the identification of the individual peaks (which nonetheless remain in the sequence shown by the Pharmacopoeia graphics).

The test sample is dissolved at 25 mg/mL, by accurately weighing 250 mg+/−0.1 mg of sample and diluting with 10 mL isooctane, added with 5 mg of butylhydroxytoluene, in a volumetric flask.

| Parameter | Set-point |
|---|---|
| Autosampler | Shimadzu AOC-5000 |
| Syringe | 10 uL (Liq) |
| Injection volume | 1 uL |
| Fill speed | 5 uL/s |

-continued

| Parameter | Set-point |
|---|---|
| Injection speed | 50 uL/s |
| Pre-injection delay | 500 ms |
| Post-injection delay | 500 ms |
| Gaschromatograph | Shimadzu GC 17A |
| GC-runtime | 85 min |
| Injection details | 250° C., SPLIT = 200, High pressure inject = OFF, SPLIT ratio after injection = 10 |
| Chromatographic column | BGB Analytics BGB-WAX (60 m × 0.25 mm × 0.25 µm) 100% Polyethylene glycol |
| Oven parameters | 170° C. held for 0.5 min, 1.0° C./min to 220° C., 2.5° C./min to 240° C., held for 21.5 min. |
| Carrier parameters | Helium at 1.0 mL/min, 182.1 kPa held for 0.5 min, 0.4 kPa/min to 204.0 kPa, 1.9 kPa/min to 219.0 kPa, held for 21.5 min. |
| Mass spectrometer | Shimadzu QP5050A (EI, 70 eV) (single quadrupole) |
| Scan parameters | Low m/z = 40, High m/z = 550, Det V = 1.7 kV absolute, Interface = 240° C., Threshold = 0, Interval = 0.5 s |
| Data acquisition | Solvent cut time = 3.9 min Start time = 4 min, End time = 80 min |

The peaks of PUFA_EE are identified by literature search of the mass spectra. The amount of each ethyl ester is calculated by area normalization, when necessary using appropriate correction factors.

Figure 2:
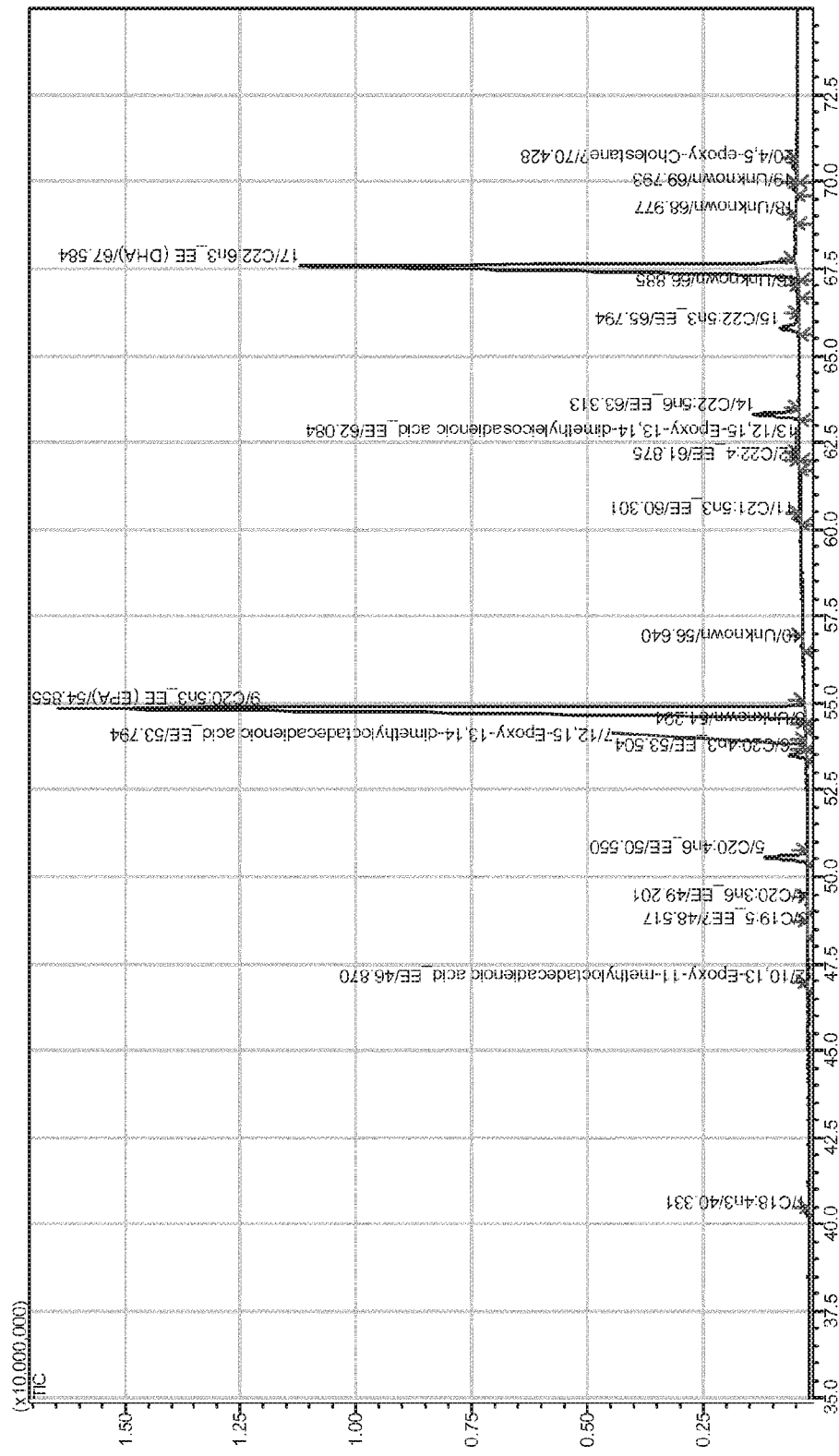
FIG. 2 shows gas chromatography combined with mass spectrometry analysis of PUFA_EE.

The GCMS chromatographic conditions are summarized as follows:

The gas chromatographic peaks of this starting batch are shown in FIG. 2, while their attribution supported by mass spectrometry, and concentrations % are reported in Table 2.

TABLE 2

| Peak No. | Ret. time [min] | Area | Area % | Library search results |
|---|---|---|---|---|
| 1 | 40.332 | 312271 | 0.10 | C18:4n3 |
| 2 | 46.870 | 494559 | 0.16 | 10,13-Epoxy-11-methyloctadecadienoic acid_EE |
| 3 | 48.517 | 218511 | 0.07 | C19:5_EE? |
| 4 | 49.201 | 298509 | 0.10 | C20:3n6_EE |
| 5 | 50.550 | 7782595 | 2.51 | C20:4n6_EE |
| 6 | 53.504 | 2822847 | 0.91 | C20:4n3_EE |
| 7 | 53.794 | 723191 | 0.23 | 12,15-Epoxy-13,14-dimethyloctadecadienoic acid_EE |
| 8 | 54.294 | 329794 | 0.11 | Unknown |
| 9 | 54.855 | 157473628 | 50.81 | C20:5n3_EE (EPA) |
| 10 | 56.640 | 464865 | 0.15 | Unknown |
| 11 | 60.301 | 933119 | 0.30 | C21:5n3_EE |
| 12 | 61.875 | 484604 | 0.16 | C22:4_EE |
| 13 | 62.084 | 679442 | 0.22 | 12,15-Epoxy-13,14-dimethyleicosadienoic acid_EE |
| 14 | 63.313 | 8014262 | 2.59 | C22:5n6_EE |
| 15 | 65.794 | 3954434 | 1.28 | C22:5n3_EE |
| 16 | 66.885 | 459514 | 0.15 | Unknown |
| 17 | 67.584 | 122269289 | 39.46 | C22:6n3_EE (DHA) |
| 18 | 68.977 | 227002 | 0.07 | Unknown |
| 19 | 69.794 | 747365 | 0.24 | Unknown |
| 20 | 70.428 | 1183869 | 0.38 | 4,5-epoxy-Cholestane? |

From the above data it emerges that the batch of PUFA_EE concerned is of excellent quality and it meets specifications of the Eu. Ph., being EPA ethyl ester=50.81% by weight and DHA ethyl ester=39.46% by weight (% ratio of areas normalized and corrected with the respective response factors). However, it contains at least 3 furan acids, which are also in the form of ethyl esters, in a quantity exceeding the limit of quantification (LOQ>0.01%) of the adopted analytical method (Gas chromatography retention times, RT: 46.87 min, 53.79 min, 62.08 min; their percentage content, 0.16, 0.23 and 0.22% respectively). These furan fatty acids, though not explicitly prohibited by the Pharmacopoeias, which indeed emphasizes its possible presence, however, did not conform to that of the declared PUFA structure, and should therefore be excluded at least from human use, either as food supplements and the like, and with even greater evidence, by the use as drugs.

Analysis of POPs shows a sum of PCDD and PCDF of 0.06 pg/g of toxic equivalents (TEQ) WHO, a cumulative sum with DL-PCBs equal to 0.28 pg/g TEQ WHO, a sum of PCB markers of 15 ng/g, a sum of PBDE of 0.44 ng/g and a sum of IPA equal to 0.1 ng/g of benzo[a]pyrene.

Similarly to the above, the results obtained on the products prepared according to the process that follows will also be presented.

Procedure

In a 4 necked flask equipped with stirrer, condenser and thermometer, 1500 mL of methanol and 750 g of urea are loaded, then heated to reflux under stirring obtaining a clear solution.

250 g of the oily mixture of PUFA_EE (weight ratio PUFA_EE:urea 1:3), weakly yellow in color, are then added, and the mixture is left under stirring for 10 min while boiling, so obtaining an opalescent solution which on resting shows little oily material on the surface.

Assuming to complete the complexation, additional 500 mL of methanol and 250 g of urea (total weight ratio PUFA_EE:urea 1:4) are added, again heating at reflux under stirring for a few minutes, and the mixture is then left to cool.

Described this operation, it is evident that the reaction will advantageously be carried out by directly using 2000 mL of methanol and 1000 g of urea for the same amount of 250 g of PUFA_EE.

Proceeding with the reaction, precipitation of the inclusion complex of PUFA_EE into urea starts at 58-60° C. When the temperature reaches 30° C., the flask is closed under nitrogen atmosphere, transferred in a refrigerator at about 5° C. and left to rest for about 20 hours (one night) with no stirring.

At the end, the precipitate is recovered by filtration on a Buchner funnel under suction, pressed well on the Buchner filter to completely remove the mother liquor, and washed thoroughly in succession with two portions, each of 300 mL of methanol solution saturated of urea and pre-cooled to +5°

C. (obtained by dissolving 160 g of urea in 1000 mL of methanol), thereby obtaining colorless washing waters.

The white crystalline precipitate is then dried at reduced temperature and pressure, obtaining 955 g of urea complex from which PUFA_EE are recovered by dissolution at about 30° C. in 2000 mL of 5% NaCl solution in water. This results in a turbid solution with a separation of an oil on the surface.

The oily phase is then extracted in succession with 2 portions of 600 mL of n-hexane and gently stirring for 10 min.

The upper organic layers are separated from the aqueous phase and gathered, then the n-hexane is evaporated to dryness to constant weight, under reduced pressure and with external heating to about 35° C., thus obtaining 210 g of a colorless oily residue, consisting of the desired PUFA_EE in the purified state, which are stored in closed container under a nitrogen atmosphere and in a refrigerator at 5° C.

The product is usually used as such, without further manipulation. Any traces of solvent may still be removed e.g. by quick molecular distillation or by extraction with supercritical fluids, both in standard conditions known to the expert; any traces of polar substances can be eliminated by quick percolation of small amounts of silica gel, eluent n-hexane, according to EP1685222.

Figure 3:
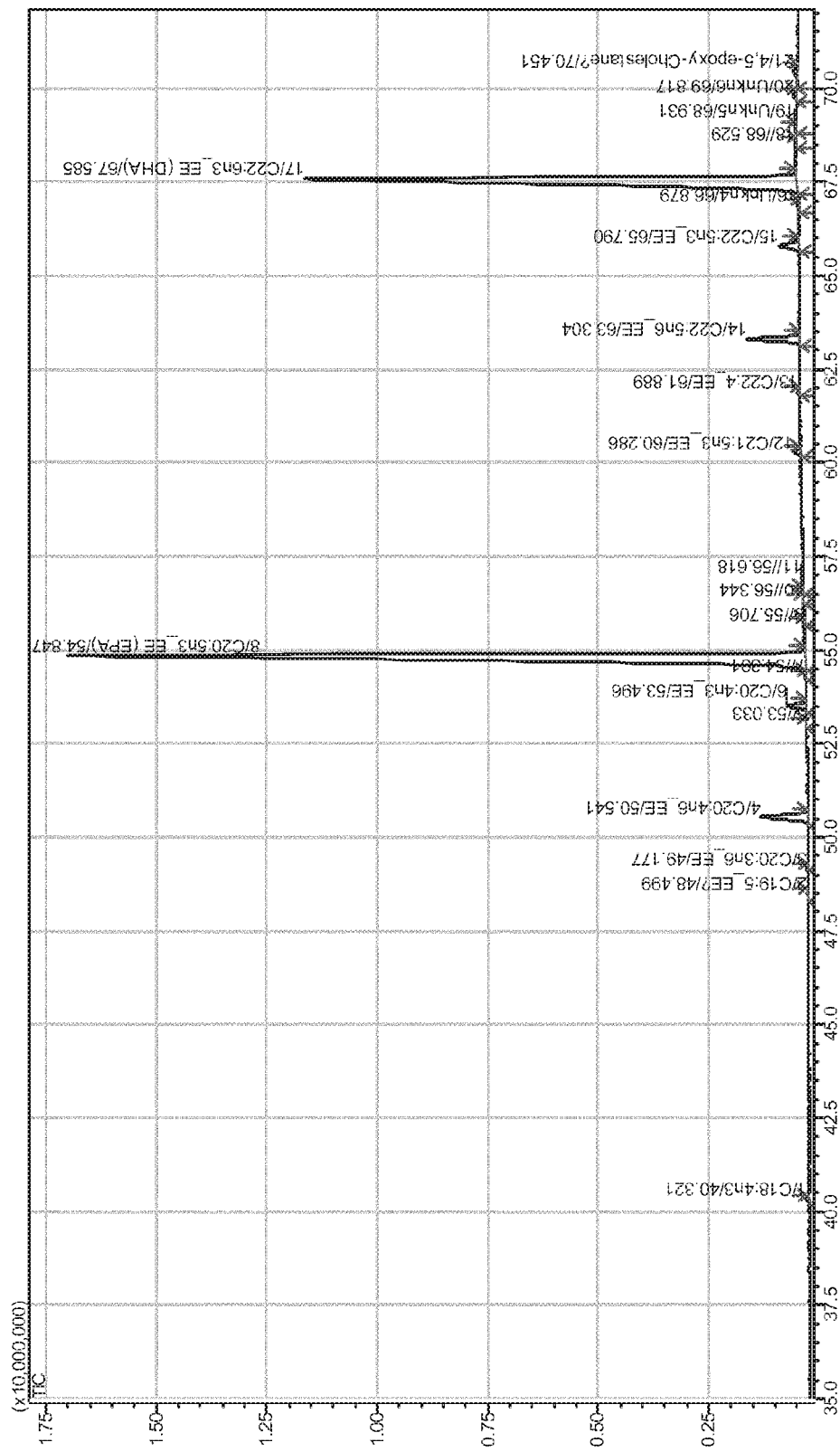
FIG. 3 shows gas chromatography combined with mass spectrometry analysis of PUFA_EE.

The product is analyzed by GCMS as described above and the gas chromatographic peaks are shown in FIG. 3, while their attribution supported by mass spectrometry, and % concentrations by weight are reported in Table 3.

TABLE 3

| Peak No. | Ret. time [min] | Area | Area % | Library search results |
|---|---|---|---|---|
| 1 | 40.321 | 350875 | 0.11 | C18:4n3 |
| 2 | 48.499 | 209102 | 0.06 | C19:5_EE? |
| 3 | 49.177 | 237939 | 0.07 | C20:3n6_EE |
| 4 | 50.541 | 9072473 | 2.72 | C20:4n6_EE |
| 5 | 53.033 | 170013 | 0.05 | Unknown |
| 6 | 53.496 | 3440930 | 1.03 | C20:4n3_EE |
| 7 | 54.301 | 334423 | 0.10 | Unknown |
| 8 | 54.847 | 166684659 | 49.94 | C20:5n3_EE (EPA) |
| 9 | 55.706 | 174468 | 0.05 | Unknown |
| 10 | 56.344 | 160782 | 0.05 | Unknown |
| 11 | 56.618 | 347039 | 0.10 | Unknown |
| 12 | 60.286 | 1094998 | 0.33 | C21:5n3_EE |
| 13 | 61.889 | 472742 | 0.14 | C22:4_EE |
| 14 | 63.304 | 9194499 | 2.75 | C22:5n6_EE |
| 15 | 65.790 | 4366628 | 1.31 | C22:5n3_EE |
| 16 | 66.880 | 488408 | 0.15 | Unknown |
| 17 | 67.585 | 134195980 | 40.21 | C22:6n3_EE (DHA) |
| 18 | 68.529 | 434518 | 0.13 | Unknown |
| 19 | 68.931 | 317571 | 0.10 | Unknown |
| 20 | 69.817 | 852795 | 0.26 | Unknown |
| 21 | 70.451 | 1147423 | 0.34 | 4,5-epoxy-Cholestane? |

The EPA ethyl ester content results to be 49.94% by weight, the content of DHA ethyl ester of 40.21% by weight.

The most obvious consideration inferred from these data refers to the total disappearance of the peaks corresponding to ethyl esters of the 3-furan fatty acids mentioned above.

The slight increase of the gas chromatographic area also argues for an at least partial elimination of the products with oligomer structure.

The values of POPs are all essentially zero.

Example 1 A

The method of Example 1 is followed, but after the initial treatment of 25 g of PUFA_EE with 100 g of urea in 200 mL of boiling methanol, the opalescent solution is added with further 25 g of urea dissolved in 50 mL of boiling methanol (total ratio by weight PUFA_EE:urea 1:5), in an attempt to complete the complexation of any still unreacted material, then heating the mixture to boiling for a further 10 min.

The method of Example 1 is still followed, and at the end the weight of the purified oily residue obtained is not proportionally increased significantly and its gas chromatographic picture is substantially equal to that obtained in accordance with Example 1.

Example 1 B

The methanol mother waters of the complexation and the washing methanol liquors obtained according to Example 1, are combined and concentrated at reduced pressure and by external heating to about 35° C. until elimination of approximately 50% of methanol and beginning of formation of a white precipitate.

To help the precipitation the mixture is kept in an ice bath for 10 minutes, then the solid precipitate is collected by filtration on a Buchner funnel under vacuum and squeezed well to completely remove the mother liquor.

The precipitate is then washed carefully with two successive portions of 100 mL of saturated solution of urea in methanol and pre-cooled to +5° C., as already described above, so to obtain colorless washing waters.

The white crystalline precipitate is then dried under vacuum to give 178 g of product from which one proceeds to the recovery of the oily inclusion material as described in Example 1, by dissolving at about 30° C. in 1000 mL of aqueous 5% NaCl, and extraction twice with 200 mL aliquots of n-hexane, under mild stirring for 10 minutes.

The upper organic phases are separated and combined, while the aqueous phase is discarded, then the n-hexane solution is concentrated to dryness under reduced pressure and bath to about 35° C., to obtain 6.0 g of an oily residue which is maintained in a container under nitrogen and at 5° C. for analytical purposes.

However, the GCMS analysis shows no gas chromatographic peak, therefore the structure of the oily material is attributed to oligomers with total absence of the ethyl esters of the individual PUFAs.

Example 1 C

Methanol mother waters and methanol washing waters obtained according to Example 1 B, are combined and concentrated at reduced pressure and by external heating to about 35° C. to dryness to give a waxy—oily semi-solid residue, that, by subsequent analysis, is shown to consist of urea, limited quantities of PUFA_EE included and not included in urea, and numerous impurities not having a PUFA_EE structure or even being totally foreign material.

From this residue it then proceeds to the total recovery of PUFA_EE and all organic material present, also the one not included in the urea complex, e.g. as described in Example 1 or 1 B, and therefore dissolving the residue at about 30° C. in 1000 mL. of aqueous 5% NaCl, and then extracting twice with 300 mL aliquots of n-hexane, under mild stirring.

The aqueous phase is then discarded, while the two upper organic phases are separated and combined, and then n-hexane is concentrated under reduced pressure to dryness on a water bath at about 35° C., obtaining 34 g of an oily-waxy residue that is kept in a container under nitrogen and at 5° C. for analytical purposes.

Figure 4:
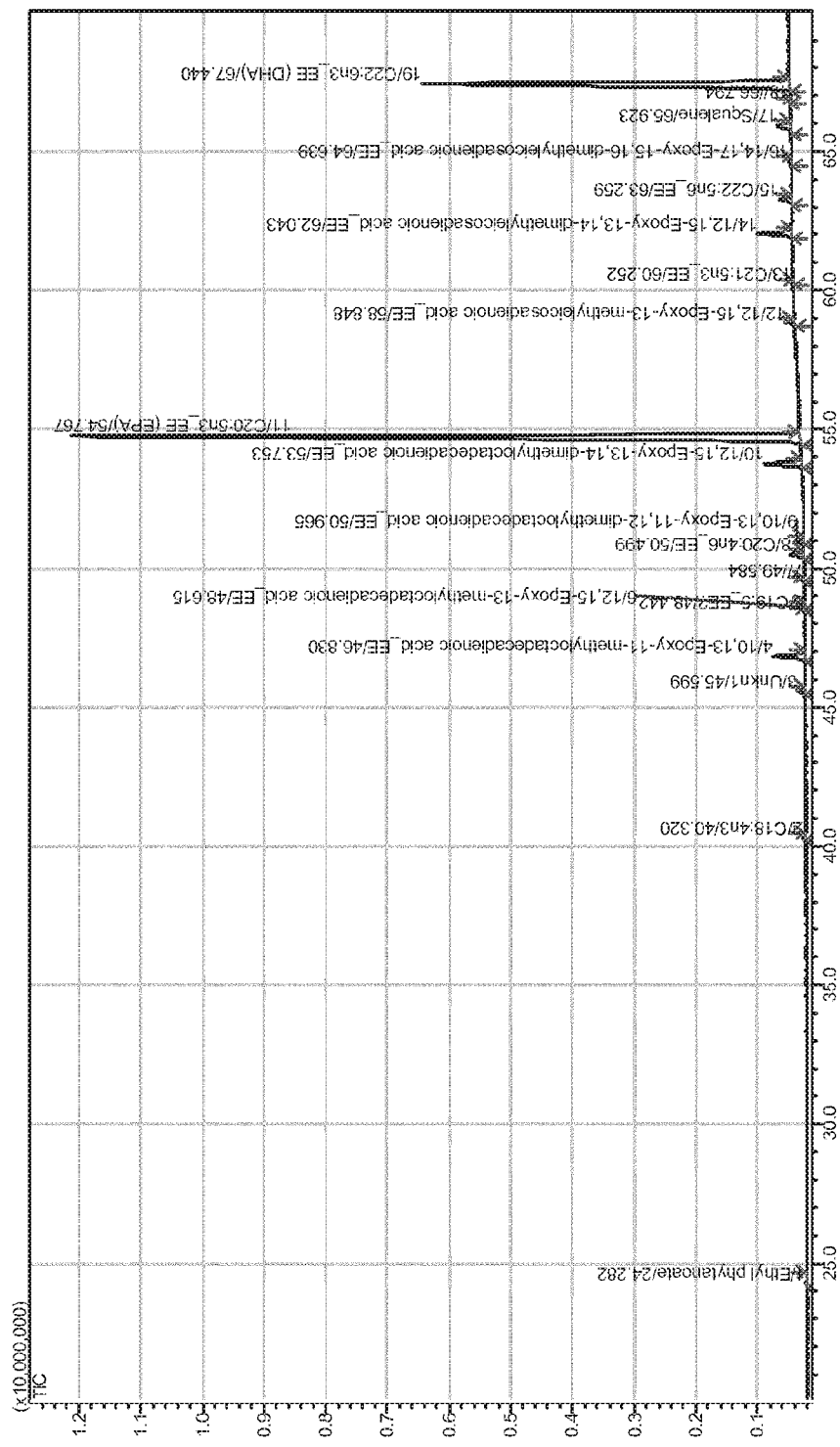
FIG. 4 shows gas chromatography combined with mass spectrometry analysis of PUFA_EE.

GCMS analysis is conducted as described above and the gas chromatographic peaks are shown in FIG. 4, while their attribution supported by mass spectrometry, and % concentrations are reported in Table 4.

TABLE 4

| Peak No. | Ret. time [min] | Area | Area % | Library search results |
|---|---|---|---|---|
| 1 | 24.282 | 317977 | 0.17 | Ethyl phytanoate |
| 2 | 40.320 | 358967 | 0.19 | C18:4n3 |
| 3 | 45.599 | 949288 | 0.51 | Unknown |
| 4 | 46.830 | 4347822 | 2.35 | 10,13-Epoxy-11-methyloctadecadienoic acid_EE |
| 5 | 48.442 | 140213 | 0.08 | C19:5_EE? |
| 6 | 48.616 | 279503 | 0.15 | 12,15-Epoxy-13-methyloctadecadienoic acid_EE |
| 7 | 49.584 | 230711 | 0.12 | Unknown |
| 8 | 50.499 | 2053514 | 1.11 | C20:4n6_EE |
| 9 | 50.966 | 904406 | 0.49 | 10,13-Epoxy-11,12-dimethyloctadecadienoic acid_EE |
| 10 | 53.753 | 5194103 | 2.81 | 12,15-Epoxy-13,14-dimethyloctadecadienoic acid_EE |
| 11 | 54.767 | 103732660 | 56.07 | C20:5n3_EE (EPA) |
| 12 | 58.848 | 968133 | 0.52 | 12,15-Epoxy-13-methyleicosadienoic acid_EE |
| 13 | 60.252 | 192585 | 0.10 | C21:5n3_EE |
| 14 | 62.043 | 4306882 | 2.33 | 12,15-Epoxy-13,14-dimethyleicosadienoic acid_EE |
| 15 | 63.259 | 1587215 | 0.86 | C22:5n6_EE |
| 16 | 64.639 | 395174 | 0.21 | 14,17-Epoxy-15,16-dimethyleicosadienoic acid_EE |
| 17 | 65.923 | 2379503 | 1.29 | Squalene |
| 18 | 66.794 | 162498 | 0.09 | Unknown |
| 19 | 67.440 | 56844015 | 30.72 | C22:6n3_EE (DHA) |

Since, however, the total GC area is greatly reduced (around −40/−45%), both with respect to the raw material, and in particular with respect to the purified fraction referred to in Example 1, these % concentrations are only expressed as % of GC individual areas with respect to the total area, without taking account of the material not revealed by the detector of the instrument (oligomers and polymers, degradation products and the like), and will have therefore only indicative meaning.

The content of EPA ethyl ester of this relatively small fraction is of 56.07%, while that of DHA ethyl ester is 30.72%.

The first and most obvious consideration deductible from the whole of GC data refers to the presence of the correspondent peaks of the 3-furan fatty acids present in the starting material (RT: 46.83 min, 53.75 min, 62.04 min; percentage content 2.35, 2.81 and 2.33% respectively) in a strongly increased concentration, with a value roughly inversely proportional to the reduced weight of the obtained fraction.

It is also evident the appearance of 4 new peaks corresponding to 4 new furan acids, not detected in the GC spectrum of the starting material evidently because their concentration was below the detection (LOD) and quantification limits (LOQ) of the analytical method (RT:48.62 min, 50.97 min, 58.85 min, 64.64 min, percentage content 0.15, 0.49, 0.52 and 0.21% respectively).

Is also found the presence of 1 GC peak identified as phytanic acid ethyl ester (RT: 24.28 min, content 0.17%): not surprising in this case the lack of detection and dosing in the starting material, since—although not explicitly prohibited in the Pharmacopoeia—the toxicity of this substance was found in recent years more and more evident and dangerous for human health, and a considerable effort on the part of some of the most well-advised producers is being made to limit their presence below the detection and quantification limit, even in spite of expensive chromatographic procedures.

Lastly, it is noted 1 peak corresponding to squalene, a long chain aliphatic hydrocarbon having formula $C_{30}H_{50}$, then not having fatty acid structure (RT: 65.92 min, content 1:29%), it also not detected in the starting product because of a concentration lower than the detection limit.

Analysis of POPs leads to a sum of PCDD and PCDF of 0.48 pg/g TEQ WHO, a cumulative sum with DL-PCBs of 2.3 pg/g TEQ WHO, a sum of the marker PCBs of 118 ng/g (0.118 ppm), a sum of PBDEs of 3.1 ng/g and finally of substances related to benzo[a]pyrene of 0.7 ng/g.

This fraction, or similar fractions, are usually discarded, but can also be used—if required—for the recovery of very moderate amounts of ethyl esters of EPA and/or DHA, and for the isolation of other byproducts such as ethyl phytanate and ethyl esters of furan fatty acids to be used for special purposes.

In the absence of any interest to the recovery of such substances, the purification process will avoid—in addition to what is described in Example 1 A—also the phases of Examples 1 B and 1C, and will therefore limit to the only procedure of Example 1 with an evident simplification of the procedure and reduction in the related costs.

Example 2

It was used the same lot of ethyl esters of omega-3 acids that was used in Example 1 (GC peaks shown in FIG. 2, attribution of the peaks and % concentrations by weight reported in Tab. 2), so also it is used the same analytical method. Also the procedure is somewhat similar, with some variants suggested by the use of ethanol as a solvent, which results to have greatly reduced solvent capacity.

Procedure 400 mL of ethanol and 75 g of urea are loaded in a flask, then heated to reflux under stirring obtaining a substantial solution with low-urea still undissolved.

Then 25 g of the oily mixture of PUFA_EE (weight ratio PUFA:urea 1:3) are added, and the mixture is then left under stirring and boiling still for 10 min, obtaining a yellowish mixture with little residual suspension.

It is left to cool under stirring and at 65° C. the desired complex starts to precipitate. At 30° C., the flask is closed under nitrogen and placed in a refrigerator at about 5° C., at rest for one night to complete the precipitation.

At the end, the precipitate is collected by filtration on a Buchner funnel, well squeezed to remove the most of the mother liquor and thoroughly washed with 2 portions of 50 mL of a saturated solution of urea in ethanol, pre-cooled to +5° C. (obtained by dissolving 30 g of urea in 200 mL of ethanol), thus obtaining at the end colorless washing waters.

After drying, 74.6 g of white crystalline precipitate are then obtained, from which one proceeds to the recovery of purified PUFA_EE by dissolution at about 30° C. in 200 mL of 5% solution of NaCl in water and subsequent extraction with 2 portions each of 100 mL of n-hexane.

The 2 organic phases are separated from the aqueous phase and pooled, then n-hexane is evaporated to dryness at about 35° C. and at reduced pressure until constant weight, obtaining 11.9 g of colorless oily residue consisting of purified PUFA_EE that are stored at around 5° C. in a nitrogen atmosphere.

The product is usually used as such. Any traces of solvents or polar impurities can be eliminated, if desired, by known methods as reported in Example 1.

The GCMS analysis shows that the composition is entirely similar to that already described in FIG. 3 and in Table 3. In particular the total absence of the 3 ethyl esters of furan acids present in the starting raw material is confirmed.

Example 2 A

The ethanol mother liquors isolated by filtration of the inclusion complex of PUFA_EE into urea, pooled with the washing ethanol as described above in Example 2, are concentrated at about 35° C. and at reduced pressure to elimination of approximately 50% of the ethanol, obtaining only traces of precipitate.

Additional 25 g of urea (total weight ratio PUFA:urea, referred to the initial reaction situation, of 1:4) are then added and the mixture brought to boiling for 10 minutes under slow stirring to obtain complete solution.

It is then allowed to cool under stirring, obtaining at about 60° C. a start of precipitation, and then to stand overnight in a refrigerator at about 5° C.

At the end the precipitate is filtered on a Buchner filter, squeezed to totally eliminate the mother liquors, and washed well with 2 portions of 50 mL of a solution saturated of urea in ethanol and pre-cooled to +5° C., such as described in Example 2.

After drying, 34.5 g of white precipitate are thus obtained, from which PUFA_EE are recovered essentially as described in Example 2, by dissolution in 200 mL of aqueous 5% solution of NaCl and extraction with 2 portions of 100 mL of n-hexane.

The evaporation to dryness of the n-hexane extracts according to Example 2 leads to a further colorless oily residue of 5.8 g, it also constituted by purified PUFA_EE, which is stored at 5° C. under nitrogen.

The GCMS analysis confirms the purity of the product, and shows that its composition is essentially the same as described in FIG. 3 and in Table 3, therefore the product is pooled to that of Example 2, thus leading to a total yield of 17.7 g.

The analysis of POPs shows that their content is "essentially zero".

Example 2 B

The ethanolic mother waters and the ethanol wash of the previous phase is concentrated to dryness under reduced pressure and at a temperature of about 35° C., then the waxy solid residue obtained is treated with an aqueous 5% solution of NaCl and extracted twice with n-hexane, essentially by the procedure of Example 1 C, in order to recover any eventual PUFA_EE still present, and included into urea, as well as other materials, also other than PUFAs, not included into urea.

At the end, the aqueous phase is discarded, while for evaporation to dryness of the n-hexane 8.2 g of waxy solid residue are recovered and stored at +5° C. under nitrogen for analytical purposes and for eventual recovery of particular substances.

In comparison with the data reported in Example 1 C, the GCMS analysis showed a reduction of the GC area significantly lower, of the order of 10%, showing that a greater amount of esters of EPA and DHA remained in this fraction containing the impurities resulting from the purification process, as also shown by the weight of 8.2 g with respect to 3.6 g of Example 1 C, that is approximately 2.3 times greater.

The ratio of the GC areas shows that EPA ester content is 56.94% and the content of DHA ester 34.68%.

The picture of foreign impurities proves almost perfectly superimposable to that of Example 1 C, except that their concentration proves to be approximately 2.3 times lower due to the greater dilution.

Ethyl esters of 3-furan fatty acids are thus revealed at 44.91 min (0.71%), 51.83 min (0.91%), and 60.10 min (0.83%), already highlighted in the raw material, and esters of other 3 furan acids at 48.93 min (0.16%), 57.11 min (0.18%), 62.46 min (0.09%), while the only ester at RT of 48.62 min according to Example 1 C, remains in this case below the limit of detection.

Ethyl phytanate was also evidenced at 23:21 min (0.03%) and squalene at 63.64 min (0.70%).

Even POPs demonstrate a concentration 2-3 times higher than that of the raw starting material, without, however, reaching that of the fraction of Example 1 C.

Example 3 (According to Literature)

A batch of ethyl esters of omega-3 acids at medium concentration is used for the purification.

It is well known that the PUFA starting concentration depends on their production source, and e.g. fish oils usually have a maximum content of omega-3 of 20-30%, a typical product having 18% EPA and 12% DHA. A quite rough indication includes saturated, monounsaturated, and n-3—in small amount n-6-polyunsaturated acids, each class roughly amounting to one-third of the composition.

After transesterification or hydrolysis, compositions at medium concentration are obtained, e.g. by distillation of low-boiling fractions or by partially selective complexation of saturated and monounsaturated components, and/or less unsaturated components than EPA and DHA, with moderate amounts of urea.

In this Example 3 a lot of ethyl esters of omega-3 acids (batch 065/07) in apparent agreement with one of the compositions indicated by the monograph 2063 of Eu.Ph. 6.3 (omega-3-acid ethyl esters 60) is used, containing in the form of ethyl esters EPA 36.1% and DHA 26.9%, measured as the ratio of their GC areas compared to the total area. These data, decreased by the areas resulting from specific "size exclusion" chromatography, correspond respectively to 33.0% and 24.6% by weight.

Other components are saturated C18:0 (0.6%), monounsaturated such as C18:1 n9 (6.9%), C18:1 n7 (2.7%), C20:1 n9 (2.0%), C22:1 n11 (1.7%), and polyunsaturated components such as C18:2 n6 (1.1%), C18:3 n3 (0.7%), C18:4 n 3 (2.0%), C20:4 n6 (2.4%), C20:4 n 3 (1.9%), C21:5 n3 (1.7%), C22:5 n6 (0.8%) and C22:5 n3 (5.2%).

The many other components are all less than 0.5%.

Ethyl esters of the 3 furan acids are detected also in this sample, already highlighted in the lot used in Example 1, each at concentration of about 0.2%, and phytanic acid ethyl ester at 0.16%.

The analysis of POPs showed a sum of PCDD and PCDF of 0.56 pg/g expressed as WHO TEQ, reaching 3.6 pg/g TEQ if added to DL-PCBs, 75 ng/g of PCB markers and 5.2 ng/g of PBDE, in substantial absence of benzo[a]pyrene.

Procedure

A solution of 150 g of urea in boiling methanol is prepared and then 100 g of a mixture of ethyl esters of the above described fatty acids (weight ratio PUFA:urea 1:1.5) are added.

Proceeding in accordance with the Example 1, the mixture is cooled to about 5° C. overnight obtaining an abundant precipitate constituted by inclusion complexes in urea of various acid esters.

The precipitate is then filtered on a Buchner funnel, well squeezed to remove the mother liquors and thoroughly washed (recommendations usually absent in the descriptions of literature) with saturated methanolic solution of urea and cooled to +5° C., as in Example 1.

After drying, the precipitate is dissolved in aqueous 5% NaCl and the oil which separates is extracted twice with n-hexane, always in accordance with Example 1.

The solvent is then evaporated to obtain an oily residue of about 42 g mainly composed of ethyl esters of saturated acids, monounsaturated acids and of polyunsaturated acids less unsaturated of EPA and DHA, and comprising also 10-15% in total of esters of EPA and DHA, as demonstrated by GC analysis.

However, it is noted in this residue the total absence of the esters of 3 furan acids and phytanic acid present in the starting material, also the specific analysis confirm in addition the total absence of pesticides of the classes discussed above (POPs).

According to literature, this fraction of the product is however discarded or mostly used to recover the limited amount of esters of EPA and DHA present.

Example 3 A (According to Literature)

The methanolic mother liquors of Example 3, pooled with the washing methanol waters, are concentrated to dryness e.g. as shown in Example 1 C, and then the residue is dissolved in aqueous 5% solution of NaCl and the separated oily phase is extracted twice with n-hexane.

After removal of the aqueous phase, the organic solvent is evaporated to dryness to give 56 g of oily residue of orange-brown color comprising the PUFA esters not complexed with urea during the procedure of Example 3.

The GC analysis of this product shows a content of ethyl esters of EPA and DHA of 86.4%, corresponding to EPA 50.1% and DHA 36.3%, based on the ratio of GC areas.

However, as the total GC area is very low and the color itself of the material clearly indicates a degradation material accumulation, it is evident the need to proceed to a purification step, e.g. by molecular distillation. In conclusion, after distillation in standard literature conditions, a composition of weakly yellow color containing in the form of ethyl esters EPA 49.0% by weight and DHA 36.2% by weight, for a total of 85.2% of the weight, is obtained. The product also contains traces of esters of saturated and monounsaturated acids, and about 2% of C18:4 n 3, about 0.5% of C20:4 n 3, 1.6% of C21:5 n3 and 1.8% of C22:5 n3, in addition to 2.5% of C20:4 n6 and 0.8% of C22:5 n6.

The other components, greatly reduced in number, are each less than 0.5%, however, presenting the serious disadvantage that the ethyl ester of phytanic acid and all the esters of the furan acids are substantially in concentration almost double compared to their content in the raw material.

Even the various POPs are fully conserved and increased in inverse proportion to the weight of the obtained composition, and therefore in a concentration almost double compared to the starting product.

Example 3 B (New)

56 g of the distilled composition obtained according to Example 3A is added under stirring to a boiling solution of 224 g of urea in methanol as described in Example 1 (weight ratio PUFA:urea 1:4).

The process continues according to Example 1 and the end, after cooling, the abundant precipitate of the inclusion complex of PUFA into urea is collected by filtration. After thorough washing of the precipitate always in accordance with Example 1, the recovery of PUFA_EE is performed following the same method, finally obtaining a purified colorless oil, having substantially the same assay by weight of EPA ester equal to 49% and DHA ester equal to 36% or more (total content by weight>85%), but totally free of esters of phytanic and furan acids, as well as free of persistent organic pollutants POPs.

If desired, e.g. to remove residual traces of organic solvents, the product can be further subjected to molecular distillation or extraction with supercritical fluids. The methanol filtrate of the complexation phase, containing the various impurities, can be eliminated. If recovered for analytical purposes, e.g. according to Example 1 C, 12 g of oily material are obtained, containing about 70% of ethyl esters of EPA and DHA (which if desired can be addressed to recovery by further complexing with urea), however containing all the impurities and POPs present in the raw material, but in a concentration about 10 times higher.

Example 3 C (New)

A sample of 56 g of the crude composition of orange-brown color obtained according to Example 3 A, is treated in agreement with Example 3 B and similarly added to a boiling solution of 224 g of urea in methanol (weight ratio PUFA:urea 1:4).

By isolating and washing the inclusion complex of PUFA into urea, 48 g of PUFA_EE purified in a similar way are then recovered, in the form of an oil colorless and totally devoid of esters of phytanic and furan acids, and of persistent organic pollutants POPs.

By molecular distillation of very small amounts of low-boiling fractions, highly purified compositions e.g. containing EPA_EE 47% by weight and DHA_EE 38% by weight, or more, are obtained (total content by weight>85%, in accordance with the specification of E.P. and USP).

The other minor components, including esters of PUFA having a lower degree of unsaturation than EPA and DHA, are substantially not different from the starting product of Example 3 A.

Alternatively, the mother methanol waters as described in Example 3 A and containing 56 g of the crude PUFA composition, but without prior isolation of the same, are used and this methanol solution is heated to boiling and added with 224 g of urea (ratio by weight PUFA:urea 1:4).

Then, by proceeding as described above, a purified composition of PUFA quite comparable to that described above in this Example 3 C, is at the end obtained.

Example 3 D (New)

A sample of material containing among other components various esters of monounsaturated and polyunsaturated acids, all having low-assay, but substantially free of esters of phytanic and furan acids, and POPs, obtained according to the procedure of Example 3, is mixed with a sample of ethyl esters of EPA and DHA with a high total assay, 85% by weight or more, which is also free from the same impurities, as obtained e.g. according to Example 3 C. The ratio of the samples will be on the basis of the weights obtained during the purification steps, e.g. 42:48.

The composition of the resulting sample will be substantially equal to that of the starting product, as described in Example 3, containing as a percentage by weight EPA ethyl ester around 33.0% and DHA ethyl ester around 24.6%, but with the advantage of being highly purified, that is substantially free from ethyl esters of phytanic and furan acids, and POPs.

Also the other ester components of the minor PUFAs, will have essentially identical content.

Alternatively, it will be also possible to proceed directly to the mixture of the inclusion products, obtained e.g. according to the same Examples 3 and 3 C and thoroughly washed, and then to jointly proceed to the recovery of all included PUFAs, exemplified as EPA 33.0% and DHA 24.6% by weight, i.e. at medium concentration, and free from all already indicated impurities.

Example 3 E (New)

As a further alternative, a sample of the same batch of ethyl esters of long chain fatty acids, at medium concentration of EPA and DHA as described in Example 3, is treated in a single step with a boiling methanol solution containing urea in excess, in amounts such as to give inclusion complexes with all the esters of fatty acids present (weight ratio of fatty acid esters:urea of 1:4 or more).

From the complex precipitated by cooling, collected and washed thoroughly as already described, a colorless oily composition having essentially the same composition of the reacted sample, but totally free of ethyl esters of phytanic and furan acids and of POPs, is recovered with the usual method.

The invention claimed is:

1. Method to purify a composition from furan fatty acids or their corresponding salts or esters, said composition comprising long chain polyunsaturated fatty acids of animal and/or vegetable origin, belonging to the omega-3 and/or omega-6 series, having 2-6 double bonds and 18 or more carbon atoms, or their salts or C1-C3 alkyl esters, said method comprising:
   a) treating 1 part by weight of said composition with at least 3 parts by weight of urea in a polar or protic solvent, to obtain a solution comprising an urea complex containing said composition;
   b) cooling said solution to precipitate said urea complex and isolating said precipitate by filtration, washing it with said polar or protic solvent, previously saturated with urea;
   c) dissolving said precipitated urea complex in water and separating the oily phase formed following said dissolution, either by extraction of said oily phase with an organic solvent unmixable with water, followed by evaporation of said solvent to dryness, or by direct extraction from said inclusion urea complex by means of supercritical fluids
   obtaining a purified composition containing long chain polyunsaturated fatty acids of animal and/or vegetable origin, belonging to the omega-3 and/or omega-6 series, having 2-6 double bonds and 18 or more carbon atoms, or their salts or C1-C3 alkyl esters, wherein said purified composition comprises furan fatty acids or their corresponding salts or esters in total concentration not higher than 0.01%, that is not higher than 100 ppm,
   wherein said purified composition comprises at least one of the following:
      a phytanic acid and/or pristanic acid, or their corresponding salts or esters in total concentration not higher than 0.001%, that is not higher than 10 ppm;
      squalene in concentration not higher than 0.001%, that is not higher than 10 ppm;
      the oligomers of said long chain polyunsaturated fatty acids, or salts or esters as defined above in concentration not higher than 1.0%;
      polychlorinated dibenzo-para-dioxins (PCDDs) and polychlorinated dibenzo-furans (PCDFs) in total concentration not higher than 0.1 pg WHO-TEQ/g;
      PCDDs, PCDFs, and dioxin-like polychlorinated biphenyls (DL-PCBs), in total concentration not higher than 0.5 pg WHO-TEQ/g;
      PCB markers in total concentration not higher than 0.5 ng/g;
      polybrominated diphenyl-ethers (PBDEs) in total concentration not higher than 0.5 ng/g;
      polycyclic aromatic hydrocarbons (PAHs), expressed as benzo[a]pyrene marker substance, in total concentration not higher than 0.1 ng/g;
      persistent organic environmental pollutants (POPs), including 2,2 bis-(pdichlorophenyl)-ethane (DDE), and/or 2,2 bis-(p-chlorophenyl)-1,1-dichloroethane (DDD), and/or 2,2 bis-(p-chlorophenyl)-1,1,1-trichloroethane (DDT), and/or polybromo-biphenyls (PBBs), and/or hexachorobenzene and/or isomers of hexachloro-cyclohexane, wherein said DDE and/or DDD and/or DDT are in total concentration not higher than 0.2 ng/g, said PBBs are in total concentration not higher than 0.5 ng/g, said hexachorobenzene is in concentration not higher than 0.01 ng/g, and said isomers of hexachloro-cyclohexane are in total concentration not higher than 0.01 ng/g, and
   wherein said purified composition has a content of said polyunsaturated fatty acids, or their salts or alkyl esters, of more than 80% and wherein said phase a) is carried out once by treating 1 part by weight of said composition with 3-4 parts, by weight of urea.

2. The method according to claim 1, wherein the fatty acids derive from fish oils, aquaculture fish included, or from krill oils, or from algae and oleaginous microorganisms, or from "single cell fermentation" of selected strains of algae, and comprise eicosapentaenoic acid and/or docosahexaenoic acid, or salts or esters thereof.

3. The method according to claim 1, further comprising step d) subjecting said purified composition containing long chain polyunsaturated fatty acids having 2-6 double bonds and 18 or more carbon atoms, or their salts or C1-C3 alkyl esters, recovered in said phase c), to molecular/short path distillation or to extraction with supercritical fluids.

4. Method of treating hypertriglyceridemia characterized by >500 mg/dl triglycerides, hypertriglyceridemia characterized by >200 mg/dl triglycerides, metabolic syndrome, metabolism and obesity related defects, type-2 diabetes and hepatic dysfunctions in subjects in need thereof with a composition comprising long chain polyunsaturated fatty acids of animal and/or vegetable origin, belonging to the omega-3 and/or omega-6 series, having 2-6 double bonds and 18 or more carbon atoms, or their salts or C1-C3 alkyl esters, said composition having a content of said polyunsaturated fatty acids, or of their salts or alkyl esters, of more than 80%, said composition comprising furan fatty acids or their corresponding salts or esters in total concentration not higher than 0.01%, that is not higher than 100 ppm, and at least one of the following:
- a phytanic acid and/or pristanic acid, or their corresponding salts or esters in total concentration not higher than 0.001%, that is not higher than 10 ppm;
- squalene in concentration not higher than 0.001%, that is not higher than 10 ppm;
- the oligomers of said long chain polyunsaturated fatty acids, or salts or esters as defined in claim 1 in concentration not higher than 1.0%;
- polychlorinated dibenzo-para-dioxins (PCDDs) and polychlorinated dibenzo-furans (PCDFs) in total concentration not higher than 0.1 pg WHO-TEQ/g;
- PCDDs, PCDFs, and dioxin-like polychlorinated biphenyls (DL-PCBs), in total concentration not higher than 0.5 pg WHO-TEQ/g;
- PCB markers in total concentration not higher than 0.5 ng/g;
- polybrominated diphenyl-ethers (PBDEs) in total concentration not higher than 0.5 ng/g;
- polycyclic aromatic hydrocarbons (PAHs), expressed as benzo[a]pyrene marker substance, in total concentration not higher than 0.1 ng/g;
- persistent organic environmental pollutants (POPs), including 2,2 bis-(pdichlorophenyl)-ethane (DDE), and/or 2,2 bis-(p-chlorophenyl)-1,1-dichloroethane (DDD), and/or 2,2 bis-(p-chlorophenyl)-1,1,1-trichloroethane (DDT), and/or polybromo-biphenyls (PBBs), and/or hexachorobenzene and/or isomers of hexachloro-cyclohexane, wherein said DDE and/or DDD and/or DDT are in total concentration not higher than 0.2 ng/g, said PBBs are in total concentration not higher than 0.5 ng/g, said hexachorobenzene is in concentration not higher than 0.01 ng/g, and said isomers of hexachloro-cyclohexane are in total concentration not higher than 0.01 ng/g, and administering said composition to said patients.

5. Method of preparing monoglycerides, diglycerides and triglycerides corresponding to the purified composition according to claim 1, said method comprising reacting said purified composition with glycerol by chemical or enzymatic route.

6. The method according to claim 5, wherein the enzymatic route is carried out with a lipase.

* * * * *